United States Patent [19]

Yang et al.

[11] Patent Number: 5,512,445

[45] Date of Patent: Apr. 30, 1996

[54] METHODS FOR THE DETECTION OF CHLAMYDIA TRACHOMATIS

[75] Inventors: Yeasing Yang; Paul D. Stull, both of San Diego, Calif.; Marc Spingola, Albuquerque, N.M.

[73] Assignee: Gen-Probe Incorporated, San Diego, Calif.

[21] Appl. No.: 450,186

[22] Filed: May 25, 1995

Related U.S. Application Data

[62] Division of Ser. No. 323,257, Oct. 14, 1994.

[51] Int. Cl.$^6$ ............... C12Q 1/68; C12P 19/34; C07H 21/04

[52] U.S. Cl. ............... 435/6; 435/91.2; 536/24.3; 536/24.32

[58] Field of Search ......... 435/6, 91.2; 536/24.3–24.33, 536/23.1

[56] References Cited

U.S. PATENT DOCUMENTS

| | | | |
|---|---|---|---|
| 4,683,195 | 7/1987 | Mullis | 435/6 |
| 4,851,330 | 7/1989 | Kohne | 435/6 |
| 5,030,557 | 7/1991 | Hogan et al. | 435/6 |
| 5,079,351 | 1/1992 | Sninsky et al. | 536/24.32 |
| 5,185,439 | 2/1993 | Arnold et al. | 536/24.3 |
| 5,232,829 | 8/1993 | Longiaru et al. | 435/6 |
| 5,252,723 | 10/1993 | Bhatt | 536/25.3 |
| 5,283,174 | 2/1994 | Arnold, Jr. et al. | 435/6 |

FOREIGN PATENT DOCUMENTS

| | | |
|---|---|---|
| 0313219 | 4/1989 | European Pat. Off. . |
| 0408295 | 1/1991 | European Pat. Off. . |
| 0420260 | 4/1991 | European Pat. Off. . |
| 8803597 | 6/1988 | WIPO . |
| WO8803957 | 6/1988 | WIPO . |
| 8810315 | 12/1988 | WIPO . |
| 8901050 | 2/1989 | WIPO . |
| 8902476 | 3/1989 | WIPO . |
| WO98902467-A | 3/1989 | WIPO . |
| 9015159 | 12/1990 | WIPO . |
| WO901519A | 12/1990 | WIPO . |
| 9322461 | 11/1993 | WIPO . |
| 9403472 | 2/1994 | WIPO . |
| WO9403472 | 2/1994 | WIPO . |

OTHER PUBLICATIONS

Bobo et al., Diagnosis of *Chlamydia trachomatis* cervical infection by detection of amplified DNA with an enzyme immunoassay. *J. Clin. Microbiol.* 28:1968–197 (1990).

Cheema et al., RNA–directed molecular hybridization screening: evidence for inapparent chlamydial infection. *Amer. J. Med. Sci.* 302:261–268 (1991).

Claas et al., Diagnostic value of the polymerase chain reaction for chlamydia detection as determined in a follow–up study. *J. Clin. Microbiol.* 29:42–45 (1991).

Claas et al., Detection of *Chlamydia trachomatis* in clinical specimens by the polymerase chain reaction. *Eur. J. Clin. Microbiol Infec. Dis.* 9:864–868 (1990).

Dutilh et al., Specific amplification of a DNA sequence common to al *Chlamydia trachomatis* serovars using the polymerase chain reaction. *Res. Microbiol.* 140:7–16 (1989).

Griffais et al., Detection of *Chlamydia trachomatis* by the polymerase chain reaction. *Res. Microbiol.* 140:139–141 (1989).

Holland et al., Detection and differentiation of *Chlamydia trachomatis, Chlamydia psittaci*, and *Chlamydia pneumoniae* by DNA amplification. *J. Infec. Dis.* 162:984–987 (1990).

Holland et al., Demonstration of Chlamydial RNA and DNA during a culture–negative state. *Infec. Immun.* 60:2040–2047 (1992).

Hyppia et al., Analysis and detection of chlamydial DNA. *J. Gen. Microbiol.* 130:3159–64 (1984).

Kluytmans et al., Performance of a nonisotopic DNA probe for detection of *Chlamydia trachomatis* in urogenital specimens. *J. Clin. Microbiol.* 29:2685–2689 (1991).

Lane et al., Rapid determination of 16S ribosomal RNA sequences for phylogenetic analyses. *Proc. Natl. Acad. Sci.* 82:6955 (1985).

McGarity et al., Deoxyribonucleic acid amplification and hybridisation in Crohn's disease using a chlamydial plasmid probe. *Gut* 32:1011–1015 (1991).

Naher et al., Evaluation of a radioctive rRNA–cDNA–hybridisation assay for the direct detection of *Chlamydia trachomatis* in urogential specimens. *Genitourin, Med.* 65:319–322 (1989).

Ossewaarde et al., Development and clinical evaluation of a polymerase chain reaction test for detection of *Chlamydia trachomatis*. *J. Clin. Microbiol.* 30:2122–2128 (1992).

Ostergaard, et al., Use of polymerase chain reaction for detection of *Chlamydia trachomatis*. *J. Clin. Microbiol.* 28:1254–1260 (1990).

Palmer et al., Detection of *Chlamydia trachomatis* by the polymerase chain reaction in swabs and urine from men with non–gonococcal urethritis. *J. Clin. Pathol.* 44:321–325 (1991).

Pollard et al., A polymerase chain reaction (PCR) protocol for the specific detection of Chlamydia spp. *Mol. Cell. Probes* 3:383–389 (1989).

Roosendaal et al., Comparison of different primer sets for the detection of *Chlamydia trachomatis* by the polymerase chain reaction. *J. Med. Microbiol.* 38:426–433 (1993).

Scieux et al., DNA fingerprinting of *Chlamydia trachomatis* by use of ribosomal RNA, oligonucleotide and randomly cloned DNA probes. *Res. Microbiol.* 143:755–765 (1992).

Pollard et al, Molecular and Cellular Probes 3: 383–389, 1989.

Dutilh et al. Res. Microbiol 140: 7–16, 1989.

*Primary Examiner*—W. Gary Jones
*Assistant Examiner*—Dianne Rees
*Attorney, Agent, or Firm*—Carlos A. Fisher

[57] ABSTRACT

Oligonucleotides and methods for the amplification and specific detection of *Chlamydia trachomatis*. The invention relates to amplification oligonucleotides capable of amplifying *Chlamydia trachomatis* nucleotide sequences and to probes and helper oligonucleotides for the specific detection of *Chlamydia trachomatis* nucleic acids. The invention also relates to methods for using the oligonucleotides of the present invention and specific combinations and kits useful for the detection of *Chlamydia trachomatis*.

54 Claims, No Drawings

SEQUENCE LISTING ( 1 ) GENERAL INFORMATION:

( i i i ) NUMBER OF SEQUENCES: 109

( 2 ) INFORMATION FOR SEQ ID NO:1:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) SEQUENCE DESCRIPTION: SEQ ID NO:1:

AGAGTCCGTA GAGCGATGAG AACG 24

( 2 ) INFORMATION FOR SEQ ID NO:2:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) SEQUENCE DESCRIPTION: SEQ ID NO:2:

GTTAGTAGGC AAATCCGCTA ACATAAGATC AGG 33

( 2 ) INFORMATION FOR SEQ ID NO:3:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) SEQUENCE DESCRIPTION: SEQ ID NO:3:

CCCGTAGACG AAAGGAGAGA AAGACCG 27

( 2 ) INFORMATION FOR SEQ ID NO:4:

( i ) SEQUENCE CHARACTERISTICS:
( A ) LENGTH: 22 base pairs
( B ) TYPE: nucleic acid
( C ) STRANDEDNESS: single ( D ) TOPOLOGY: linear ( i i ) SEQUENCE DESCRIPTION: SEQ ID NO:4:

CCCGAAGATT CCCCTTGATC GC 22

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:5:

CGGAGTAAGT TAAGCACGCG GACGATTGGA 30

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CGGAGTAAGT TAAGCACGCG GACGATTGGA AGA 33

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:7:

GTCTAGTCCT ACTCAGGTGT TGAG 24

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:8:

CCTAGTTGAA CACATCTGGA AAGATGGATG ATA 33

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:9:

CGTTCTCATC GCTCTACGGA CTCT 24

( 2 ) INFORMATION FOR SEQ ID NO:10:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:10:

CGGTCTTTCT CTCCTTTCGT CTACGGG 27

( 2 ) INFORMATION FOR SEQ ID NO:11:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:11:

CCTGATCTTA TGTTAGCGGA TTTGCCTACT AAC 33

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:12:

GCGATCAAGG GGAATCTTCG GG 22

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:13:

TCCAATCGTC CGCGTGCTTA ACTTACTCCG 30

( 2 ) INFORMATION FOR SEQ ID NO:14:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:14:

TCTTCCAATC GTCCGCGTGC TTAACTTACT CCG 33

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:15:

CTCAACACCT GAGTAGGACT AGAC 24

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:16:

TATCATCCAT CTTTCCAGAT GTGTTCAACT AGG                    33

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) SEQUENCE DESCRIPTION: SEQ ID NO:17:

CGCGTCTAGT CCTACTCAGG TGTTG                              25

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) SEQUENCE DESCRIPTION: SEQ ID NO:18:

CCCCAGATTC AGACTAGG                                      18

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) SEQUENCE DESCRIPTION: SEQ ID NO:19:

CGGTCATTGA CTAGTATTTA GCCTT                              25

(2) INFORMATION FOR SEQ ID NO:20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) SEQUENCE DESCRIPTION: SEQ ID NO:20:

TTTCTTCATA GTACTGGTTC ACT                                23

(2) INFORMATION FOR SEQ ID NO:21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) SEQUENCE DESCRIPTION: SEQ ID NO:21:

ATTTCACTCC CTTAACAAGG GTT                                23

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) SEQUENCE DESCRIPTION: SEQ ID NO:22:

TTGTAAGCTA CAGGTTTCAG GT                                 22

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:23:

ACGGGCAATT GGTCTGCGAC C           21

( 2 ) INFORMATION FOR SEQ ID NO:24:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:24:

AGCAAAGACC CGGAGGTCCG AAT           23

( 2 ) INFORMATION FOR SEQ ID NO:25:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:25:

GAATACATAG GTATGCAAAG CGA           23

( 2 ) INFORMATION FOR SEQ ID NO:26:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:26:

CCTGCCGAAC TGAAACATCT TAGT           24

( 2 ) INFORMATION FOR SEQ ID NO:27:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:27:

CAGAGGAAAA GAAATCGAAG AGAT           24

( 2 ) INFORMATION FOR SEQ ID NO:28:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:28:

TGTAGGATTG AGGATAAAGG AT           22

( 2 ) INFORMATION FOR SEQ ID NO:29:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) SEQUENCE DESCRIPTION: SEQ ID NO:29:

GGACTCCTAG TTGAACACAT CTGGAAAGA                    29

( 2 ) INFORMATION FOR SEQ ID NO:30:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:30:

CAACACCTGA GTAGGACTAG ACGCG                        25

( 2 ) INFORMATION FOR SEQ ID NO:31:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:31:

CCTAGTCTGA ATCTGGGG                                18

( 2 ) INFORMATION FOR SEQ ID NO:32:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:32:

AAGGCTAAAT ACTAGTCAAT GACCG                        25

( 2 ) INFORMATION FOR SEQ ID NO:33:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:33:

AGTGAACCAG TACTATGAAG AAA                          23

( 2 ) INFORMATION FOR SEQ ID NO:34:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:34:

AACCCTTGTT AAGGGAGTGA AAT                          23

( 2 ) INFORMATION FOR SEQ ID NO:35:

( i ) SEQUENCE CHARACTERISTICS:

( A ) LENGTH: 22 base pairs
( B ) TYPE: nucleic acid
( C ) STRANDEDNESS: single
( D ) TOPOLOGY: linear ( i i ) SEQUENCE DESCRIPTION: SEQ ID NO:35:

ACCTGAAACC TGTAGCTTAC AA 22

( 2 ) INFORMATION FOR SEQ ID NO:36:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) SEQUENCE DESCRIPTION: SEQ ID NO:36:

GGTCGCAGAC CAATTGCCCG T 21

( 2 ) INFORMATION FOR SEQ ID NO:37:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) SEQUENCE DESCRIPTION: SEQ ID NO:37:

ATTCGGACCT CCGGGTCTTT GCT 23

( 2 ) INFORMATION FOR SEQ ID NO:38:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) SEQUENCE DESCRIPTION: SEQ ID NO:38:

TCGCTTTGCA TACCTATGTA TTC 23

( 2 ) INFORMATION FOR SEQ ID NO:39:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) SEQUENCE DESCRIPTION: SEQ ID NO:39:

ACTAAGATGT TTCAGTTCGG CAGG 24

( 2 ) INFORMATION FOR SEQ ID NO:40:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) SEQUENCE DESCRIPTION: SEQ ID NO:40:

ATCTCTTCGA TTTCTTTTCC TCTG 24

( 2 ) INFORMATION FOR SEQ ID NO:41:

( i ) SEQUENCE CHARACTERISTICS:
( A ) LENGTH: 22 base pairs
( B ) TYPE: nucleic acid ( C ) STRANDEDNESS: single
( D ) TOPOLOGY: linear ( i i ) SEQUENCE DESCRIPTION: SEQ ID NO:41:

ATCCTTTATC CTCAATCCTA CA                                                                22

( 2 ) INFORMATION FOR SEQ ID NO:42:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:42:

TCTTTCCAGA TGTGTTCAAC TAGGAGTCC                                                         29

( 2 ) INFORMATION FOR SEQ ID NO:43:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:43:

AATTAATAC GACTCACTAT AGGGAGA                                                            27

( 2 ) INFORMATION FOR SEQ ID NO:44:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

TGTCCTTAAC TTGGGAATAA CGGTTGGAA                                                         29

( 2 ) INFORMATION FOR SEQ ID NO:45:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:45:

TTCCAACCGT TATTCCCAAG TTAAGGACA                                                         29

( 2 ) INFORMATION FOR SEQ ID NO:46:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:46:

CCGAATGTGG CGATATTTGG GCATCC                                                            26

( 2 ) INFORMATION FOR SEQ ID NO:47:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:47:

GGATGCCCAA ATATCGCCAC ATTCGG 26

( 2 ) INFORMATION FOR SEQ ID NO:48:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:48:

GAGTAACGTT AAAGAAGGGG ATCTTAGG 28

( 2 ) INFORMATION FOR SEQ ID NO:49:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:49:

CCTAAGATCC CCTTCTTTAA CGTTACTC 28

( 2 ) INFORMATION FOR SEQ ID NO:50:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:50:

GGCCTTTACC CCACCAACTA GCTGATA 27

( 2 ) INFORMATION FOR SEQ ID NO:51:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:51:

TATCAGCTAG TTGGTGGGGT AAAGGCC 27

( 2 ) INFORMATION FOR SEQ ID NO:52:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:52:

AGAGUCCGUA GAGCGAUGAG AACG 24

( 2 ) INFORMATION FOR SEQ ID NO:53:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:53:

GUUAGUAGGC AAAUCCGCUA ACAUAAGAUC AGG 33

( 2 ) INFORMATION FOR SEQ ID NO:54:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:54:

CCCGUAGACG AAAGGAGAGA AAGACCG 27

( 2 ) INFORMATION FOR SEQ ID NO:55:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:55:

CCCGAAGAUU CCCCUUGAUC GC 22

( 2 ) INFORMATION FOR SEQ ID NO:56:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:56:

CGGAGUAAGU UAAGCACGCG GACGAUUGGA 30

( 2 ) INFORMATION FOR SEQ ID NO:57:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:57:

CGGAGUAAGU UAAGCACGCG GACGAUUGGA AGA 33

( 2 ) INFORMATION FOR SEQ ID NO:58:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:58:

GUCUAGUCCU ACUCAGGUGU UGAG 24

( 2 ) INFORMATION FOR SEQ ID NO:59:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:59:

CCUAGUUGAA CACAUCUGGA AAGAUGGAUG AUA 33

( 2 ) INFORMATION FOR SEQ ID NO:60:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:60:

CGUUCUCAUC GCUCUACGGA CUCU        24

( 2 ) INFORMATION FOR SEQ ID NO:61:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:61:

CGGUCUUUCU CUCCUUUCGU CUACGGG        27

( 2 ) INFORMATION FOR SEQ ID NO:62:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:62:

CCUGAUCUUA UGUUAGCGGA UUUGCCUACU AAC        33

( 2 ) INFORMATION FOR SEQ ID NO:63:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:63:

GCGAUCAAGG GGAAUCUUCG GG        22

( 2 ) INFORMATION FOR SEQ ID NO:64:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:64:

UCCAAUCGUC CGCGUGCUUA ACUUACUCCG        30

( 2 ) INFORMATION FOR SEQ ID NO:65:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:65:

UCUUCCAAUC GUCCGCGUGC UUAACUUACU CCG        33

( 2 ) INFORMATION FOR SEQ ID NO:66:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:66:

```
CUCAACACCU  GAGUAGGACU  AGAC                                24
```

( 2 ) INFORMATION FOR SEQ ID NO:67:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:67:

```
UAUCAUCCAU  CUUCCAGAU  GUGUUCAACU  AGG                      33
```

( 2 ) INFORMATION FOR SEQ ID NO:68:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:68:

```
CGCGUCUAGU  CCUACUCAGG  UGUUG                               25
```

( 2 ) INFORMATION FOR SEQ ID NO:69:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:69:

```
CCCCAGAUUC  AGACUAGG                                        18
```

( 2 ) INFORMATION FOR SEQ ID NO:70:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:70:

```
CGGUCAUUGA  CUAGUAUUUA  GCCUU                               25
```

( 2 ) INFORMATION FOR SEQ ID NO:71:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:71:

```
UUUCUUCAUA  GUACUGGUUC  ACU                                 23
```

( 2 ) INFORMATION FOR SEQ ID NO:72:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) SEQUENCE DESCRIPTION: SEQ ID NO:72:

AUUUCACUCC CUUAACAAGG GUU    23

( 2 ) INFORMATION FOR SEQ ID NO:73:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) SEQUENCE DESCRIPTION: SEQ ID NO:73:

UUGUAAGCUA CAGGUUUCAG GU    22

( 2 ) INFORMATION FOR SEQ ID NO:74:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) SEQUENCE DESCRIPTION: SEQ ID NO:74:

ACGGGCAAUU GGUCUGCGAC C    21

( 2 ) INFORMATION FOR SEQ ID NO:75:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) SEQUENCE DESCRIPTION: SEQ ID NO:75:

AGCAAAGACC CGGAGGUCCG AAU    23

( 2 ) INFORMATION FOR SEQ ID NO:76:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) SEQUENCE DESCRIPTION: SEQ ID NO:76:

GAAUACAUAG GUAUGCAAAG CGA    23

( 2 ) INFORMATION FOR SEQ ID NO:77:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) SEQUENCE DESCRIPTION: SEQ ID NO:77:

CCUGCCGAAC UGAAACAUCU UAGU    24

( 2 ) INFORMATION FOR SEQ ID NO:78:

( i ) SEQUENCE CHARACTERISTICS:
    ( A ) LENGTH: 24 base pairs ( B ) TYPE: nucleic acid
( C ) STRANDEDNESS: single
( D ) TOPOLOGY: linear ( i i ) SEQUENCE DESCRIPTION: SEQ ID NO:78:

CAGAGGAAAA GAAAUCGAAG AGAU                                    24

( 2 ) INFORMATION FOR SEQ ID NO:79:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) SEQUENCE DESCRIPTION: SEQ ID NO:79:

UGUAGGAUUG AGGAUAAAGG AU                                      22

( 2 ) INFORMATION FOR SEQ ID NO:80:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) SEQUENCE DESCRIPTION: SEQ ID NO:80:

GGACUCCUAG UUGAACACAU CUGGAAAGA                               29

( 2 ) INFORMATION FOR SEQ ID NO:81:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) SEQUENCE DESCRIPTION: SEQ ID NO:81:

CAACACCUGA GUAGGACUAG ACGCG                                   25

( 2 ) INFORMATION FOR SEQ ID NO:82:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) SEQUENCE DESCRIPTION: SEQ ID NO:82:

CCUAGUCUGA AUCUGGGG                                           18

( 2 ) INFORMATION FOR SEQ ID NO:83:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) SEQUENCE DESCRIPTION: SEQ ID NO:83:

AAGGCUAAAU ACUAGUCAAU GACCG                                   25

( 2 ) INFORMATION FOR SEQ ID NO:84:

( i ) SEQUENCE CHARACTERISTICS:
( A ) LENGTH: 23 base pairs
( B ) TYPE: nucleic acid
( C ) STRANDEDNESS: single ( D ) TOPOLOGY: linear ( i i ) SEQUENCE DESCRIPTION: SEQ ID NO:84:

AGUGAACCAG UACUAUGAAG AAA                                         23

( 2 ) INFORMATION FOR SEQ ID NO:85:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:85:

AACCCUUGUU AAGGGAGUGA AAU                                         23

( 2 ) INFORMATION FOR SEQ ID NO:86:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:86:

ACCUGAAACC UGUAGCUUAC AA                                          22

( 2 ) INFORMATION FOR SEQ ID NO:87:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:87:

GGUCGCAGAC CAAUUGCCCG U                                           21

( 2 ) INFORMATION FOR SEQ ID NO:88:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:88:

AUUCGGACCU CCGGGUCUUU GCU                                         23

( 2 ) INFORMATION FOR SEQ ID NO:89:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:89:

UCGCUUUGCA UACCUAUGUA UUC                                         23

( 2 ) INFORMATION FOR SEQ ID NO:90:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:90:

ACUAAGAUGU UUCAGUUCGG CAGG 24

( 2 ) INFORMATION FOR SEQ ID NO:91:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:91:

AUCUCUUCGA UUUCUUUUCC UCUG 24

( 2 ) INFORMATION FOR SEQ ID NO:92:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:92:

AUCCUUUAUC CUCAAUCCUA CA 22

( 2 ) INFORMATION FOR SEQ ID NO:93:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:93:

UCUUUCCAGA UGUGUUCAAC UAGGAGUCC 29

( 2 ) INFORMATION FOR SEQ ID NO:94:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:94:

AAUUUAAUAC GACUCACUAU AGGGAGA 27

( 2 ) INFORMATION FOR SEQ ID NO:95:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:95:

UGUCCUUAAC UUGGGAAUAA CGGUUGGAA 29

( 2 ) INFORMATION FOR SEQ ID NO:96:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:96:

UUCCAACCGU UAUUCCCAAG UUAAGGACA    29

(2) INFORMATION FOR SEQ ID NO:97:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) SEQUENCE DESCRIPTION: SEQ ID NO:97:

CCGAAUGUGG CGAUAUUUGG GCAUCC    26

(2) INFORMATION FOR SEQ ID NO:98:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) SEQUENCE DESCRIPTION: SEQ ID NO:98:

GGAUGCCCAA AUAUCGCCAC AUUCGG    26

(2) INFORMATION FOR SEQ ID NO:99:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) SEQUENCE DESCRIPTION: SEQ ID NO:99:

GAGUAACGUU AAAGAAGGGG AUCUUAGG    28

(2) INFORMATION FOR SEQ ID NO:100:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) SEQUENCE DESCRIPTION: SEQ ID NO:100:

CCUAAGAUCC CCUUCUUUAA CGUUACUC    28

(2) INFORMATION FOR SEQ ID NO:101:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) SEQUENCE DESCRIPTION: SEQ ID NO:101:

GGCCUUUACC CCACCAACUA GCUGAUA    27

(2) INFORMATION FOR SEQ ID NO:102:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) SEQUENCE DESCRIPTION: SEQ ID NO:102:

UAUCAGCUAG UUGGUGGGGU AAAGGCC    27

( 2 ) INFORMATION FOR SEQ ID NO:103:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:103:

GTCGCCTGGG CCATTTCTCT GCGGCCCCC GGGG    34

( 2 ) INFORMATION FOR SEQ ID NO:104:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:104:

TCTCCCTATA GTGAGTCGTA TTAAATT    27

( 2 ) INFORMATION FOR SEQ ID NO:105:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:105:

UCUCCCUAUA GUGAGUCGUA UUAAAUU    27

( 2 ) INFORMATION FOR SEQ ID NO:106:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:106:

GAAATTAATA CGACTCACTA TAGGGAGA    28

( 2 ) INFORMATION FOR SEQ ID NO:107:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:107:

TCTCCCTATA GTGAGTCGTA TTAATTTC    28

( 2 ) INFORMATION FOR SEQ ID NO:108:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:108:

GAAAUUAAUA CGACUCACUA UAGGGAGA    28

( 2 ) INFORMATION FOR SEQ ID NO:109:

( i ) SEQUENCE CHARACTERISTICS:
   ( A ) LENGTH: 28 base pairs
   ( B ) TYPE: nucleic acid
   ( C ) STRANDEDNESS: single
   ( D ) TOPOLOGY: linear ( i i ) SEQUENCE DESCRIPTION: SEQ ID NO:109:

UCUCCCUAUA GUGAGUCGUA UUAAUUUC    2 8

METHODS FOR THE DETECTION OF *CHLAMYDIA TRACHOMATIS*

This application is a divisional of application Ser. No. 08/323,257, filed on Oct. 14, 1994.

FIELD OF THE INVENTION

The invention described and claimed herein relates to the design and use of nucleic acid probes, helper oligonucleotides and amplification oligonucleotides for amplifying and detecting nucleic acids from the bacterial species *Chlamydia trachomatis* in test samples, e.g., from throat swabs, tissue samples, body fluids, and from cultures.

BACKGROUND OF THE INVENTION

The chlamydiae are among the most common animal pathogens in the world. These Gram-negative cells are unusual among bacteria in being obligate intracellular organisms. They replicate within the infected host cell and, lacking enzymes able to produce their own energy from metabolic reactions, rob their hosts of energy by using ATP produced by the host for their own requirements.

*Chlamydia trachomatis* is one of the three species classifications of the genus Chlamydia, and is a human pathogen. See American Society for Microbiology, Manual of Clinical Microbiology (5th ed. 1991). *Chlamydia trachomatis* strains include the causal agents of trachoma, inclusion conjunctivitis, and genital tract diseases. In the latter context, *C. trachomatis* is the leading cause of sexually transmitted disease in the world, causing urethritis in men and cervicitis in women. An infected woman may transmit the infection to her child during birth, resulting in pneumonia or eye disease among other conditions. Early detection of *C. trachomatis* infection in affected individuals can accelerate necessary treatment and prevent continued transmission of the agent.

It is therefore an object of the present invention to provide nucleic acid hybridization probes for the rapid and specific detection of *C. trachomatis* in test samples and particularly in human clinical specimens.

As used herein, the term "test sample" is intended to mean any sample suspected of containing the intended target nucleic acid, and includes but is not limited to: biological samples, body fluids or exudate such as urine, blood, milk, cerebrospinal fluid, sputum, saliva, stool, lung aspirates, throat or genital swabs, clinical specimens containing one or more of the foregoing, environmental samples, food samples and laboratory samples.

Nucleic acid hybridization is the process by which two nucleic acid strands having completely or partially complementary nucleotide sequences come together under predetermined reaction conditions to form a stable, double-stranded hybrid with specific hydrogen bonds. Either nucleic acid strand may be a deoxyribonucleic acid (DNA) or a ribonucleic acid (RNA); thus hybridization can involve RNA:RNA hybrids, DNA:DNA hybrids, or RNA:DNA hybrids.

Thus, as used in this application, the term "hybridization" refers to the ability of two completely or partly complementary single nucleic acid strands to come together in an antiparallel orientation to form a stable structure having a double-stranded region. The two constituent strands of this double-stranded structure, sometimes called a hybrid, are held together with hydrogen bonds. Although these hydrogen bonds most commonly form between nucleotides containing the bases adenine and thymine or uracil (A and T or U) or cytosine and guanine (C and G), base pairing can form between bases who are not members of these "canonical" pairs. Non-canonical base pairing is well-known in the art. See e.g., *The Biochemistry of the Nucleic Acids* (Adams et al., eds., 1992).

Nucleic acid hybridization is a common method for detecting and quantitating target nucleic acids having specific nucleotide sequences. Such methods are useful for identifying and classifying organisms, diagnosing infectious diseases and genetic abnormalities, testing food and drugs, and identifying criminal suspects, among numerous other things. Typically, nucleic acid hybridization assays use a labeled oligonucleotide hybridization assay probe having a nucleic acid sequence complementary to the target sequence. Such labels are well known in the art, and may include radioactive isotopes, enzymes, or fluorescent, luminescent, or chemiluminescent groups; the Applicants prefer the use of chemiluminescent acridinium esters as labels. See Arnold et al., U.S. Pat. No. 5,185,439, which enjoys common ownership with the present application and is incorporated by reference her%in. The probe is mixed with a sample suspected of containing a nucleic acid having the target sequence under hybridization conditions suitable for allowing annealing of the two strands by hydrogen bonding in the region of complementarity. The probe then hybridizes to the target nucleic acid present in the sample. The resulting hybrid duplex may be detected by various techniques well known in the art, such as hydroxyapatite adsorption. Also included among these techniques are those that involve selectively degrading the label present on unhybridized probe and then measuring the amount of label associated with the remaining hybridized probe, as disclosed in Arnold et al., U.S. Pat. No. 5,283,174, which enjoys common ownership with the present application and is incorporated by reference herein. This latter technique, called the hybridization protection assay (HPA), is presently preferred by the Applicant.

Often a test sample will not contain a great enough number of nucleic acid molecules to permit direct detection or quantification by nucleic acid hybridization due to the sensitivity limits of the particular label used. In such a case, the amount of detectable target nucleotide sequence is increased before nucleic acid hybridization is used to identify its presence or amount in the test sample. This procedure is termed nucleic acid amplification, and the method of increasing the amount of the target nucleic acid is referred to as amplifying the target nucleic acid or target nucleotide sequence.

Amplification methods involve the use of at least one nucleic acid strand containing a target nucleotide sequence as a template in a nucleic acid polymerizing reaction to produce a complementary second strand containing the target nucleotide sequence. By repeating this process, Using the product nucleic acids as templates in subsequent cycles, the number of nucleic acid molecules having the target nucleotide sequence increases rapidly.

A number of amplification methods have been described; among these are various embodiments of the polymerase chain reaction (PCR), (see e.g., Mullis et al., U.S. Pat. No. 4,683,195), and methods which utilize in vitro transcription (RNA synthesis) in one or more step of the procedure, (see e.g., Murakawa et al., *DNA* 7:287–295, Burg et al., PCT Application No. WO89/1050, Gingeras et al., PCT Application No. WO88/10315, Kacian & Fultz, European Application No. 89313154, McDonough, et al., PCT Publication No. WO 94/03472, Kacian, et al., PCT Publication No. WO 93/22461, and Dattagupta, et al. (filed in the United States Mar. 16, 1994, U.S. application Ser. No. 08/215,081). The disclosure of these references are incorporated by reference herein; the last two of these references enjoy common ownership with the present application.

Most nucleic acid amplification methods employ oligonucleotide primers and/or promoter-primers. These primers or promoter-primers are relatively short, (preferably between 10 and 100 nucleotides; most preferably between about 12 and 50 nucleotides in length) single-stranded nucleic acid molecules which are chemically, biologically or enzymatically synthesized, designed, and/or selected through human intervention to have a nucleotide sequence complementary to at least a portion of a nucleotide sequence region of the intended target nucleic acid. When the primer or promoter-primer is brought together with the target nucleic acid under conditions which allow the two nucleic acid strands to hybridize, at least part of the primer or promoter-primer forms a double-stranded, hydrogen-bonded hybrid with the target nucleic acid. Often, but not invariably, a distinctive feature of such a hybrid is that a primer or promoter-primer has a free 3' hydroxyl group able to react with a nucleotide in a nucleic acid polymerase-mediated primer extension reaction while hybridized. However, a free 3' hydroxyl group may not be necessary for a promoter-primer to function as a promoter.

A primer extension reaction occurs when the double-stranded primer:target nucleic acid hybrid is contacted with a nucleic acid polymerase, and the necessary nucleotide triphosphates. The primer's available 3' hydroxyl group enables the nucleic acid polymerase to specifically begin adding nucleotide residues to the 3' end of the primer; hence, the nascent nucleic acid strand grows in the 5' to 3' direction relative to the primer's polarity. The sequence of the growing primer extension product is dictated by the nucleotide sequence of the target nucleic acid template. Thus, the primer initiates the synthesis of a complementary nucleic acid strand in the region of initial annealing or hybridization.

A "promoter-primer" can function as a primer, in that it has a 3' region of complementarity to its intended nucleic acid target, when it has a free 3' hydroxyl group. Additionally, a promoter-primer has a nucleotide sequence region at its 5' end which is not complementary to the target nucleic acid. When this region is made double-stranded through the action of a nucleic acid polymerase (this time extending the 3' end of the template nucleic acid), the double-stranded non-complementary region can function as an initiation site for RNA synthesis using an enzyme having RNA polymerase activity.

Depending on the uniqueness of the target nucleotide sequence and the degree of selectivity desired in a hybridization assay, a primer or promoter-primer may also or alternatively function as a hybridization assay probe. Alternatively, a hybridization assay probe or amplification oligonucleotide may be designed and used solely for its primary function.

A hybridization assay probe is used to detect and/or quantify the presence of the intended target nucleic acid; such a probe is usually labeled with a radioactive or luminescent atom or a detectable chemical group, such as a chemiluminescent moiety. The Applicant prefers using acridinium ester derivatives as a labeling reagent. Sometimes the intended target nucleic acid will include any of a population of different nucleic acid molecules with nucleotide sequences usually derived from a biological source. By way of example only, and not of limitation, the target nucleotide sequence may be shared by the nucleic acids of a genus of organisms (but not by organisms outside the genus) the detection of any of which is desired. Alternatively, the target nucleotide sequence may be unique to a species of organism or to a strain of that species.

Not all probes are necessarily labeled. Some hybridization probes, termed "helper oligonucleotides" or "helper probes", are designed to facilitate the ability of a separate labeled probe to bind to its target nucleotide sequence. Although not wishing to be bound by theory, helper probes are thought to facilitate binding of the labeled probe by locally decreasing the amount of intramolecular hydrogen-bonding in the target nucleic acid, thus making the target nucleotide sequence more available for specific hybridization with the labeled probe. Depending on the location of the labeled probe's binding site and the secondary structure of the target nucleic acid, helper probes may be directed to nucleotide sequence regions proximal to the labeled probe's binding site, or directed to regions distal from the binding site which nevertheless affect probe binding. Helper probes are described in Hogan et al., U.S. Pat. No. 5,030,557 which enjoys common ownership with the current application, and which is incorporated by reference herein.

Descriptions of the use of nucleic acid hybridization to detect the presence of particular nucleic acid sequences are given in Kohne, U.S. Pat. No. 4,851,330 and in Hogan et al., International Patent Application No. PCT/US87/03009; both of these references enjoy common ownership with the present application, and are incorporated by reference herein. Hogan describes methods for determining the presence of a non-viral organism or a group of non-viral organisms in a sample (e.g., sputum, urine, blood and tissue sections, food, soil and water) using nucleic acid hybridization techniques.

Hogan, supra, also describes a number of hybridization probes which specifically detect only targeted ribosomal RNA (rRNA) nucleotide sequences belonging to a specific organism or group of organisms.

DNA hybridization assay probes for detection of *C. trachomatis* have been described. Hyppia et al., *J. Gen. Microbiol.* 130:3159–64 (1984), describe the isolation of a 6.7 kb plasmid from *C. trachomatis* and its use as a hybridization probe. Griffais et al., *Res. Microbiol.* 140:139–141 (1989), Ostergaard, et al., *J. Clin. Microbiol.* 28:1254–1260 (1990), McGarity et al., *Gut* 32:1011–1015 (1991), Claas et al., *J. Clin. Microbiol.* 29:42–45 (1991), Longiaru, EPO 420 260, Application No. 90118620.5, and Longiaru et al., U.S. Pat. No. 5,232,829 amplified *C. trachomatis* plasmid nucleotide sequences using the polymerase chain reaction (PCR) in conjunction with amplification oligonucleotides. Amplification of sequences encoding the major outer membrane protein (MOMP) of *C. trachomatis* was described by Dutilh et al., *Res. Microbiol.* 140:7–16 (1989), Holland et al., *J. Infec. Dis.* 162:984–987 (1990), Bobo et al., *J. Clin. Microbiol.* 28:1968–197 (1990), Holland et al., *Infec. Immun.* 60:2040–2047 (1992), and Palmer et al., *J. Clin. Pathol.* 44:321–325 (1991). Ossewaarde et al., *J. Clin. Microbiol.* 30:2122–2128 (1992) and Roosendaal et al., *J. Med. Microbiol.* 38:426–433 (1993) describe amplification of plasmid and MOMP sequences.

Hogan et al., PCT Application Number PCT/US87/03009, which enjoys common ownership with the present application, and Shah et al., PCT Publication Number WO90/15159, describe probes for the detection of *C. trachomatis*

16S and 23S rRNA sequences. Naher et al., *Genitourin. Med.* 65:319–322 (1989), Kluytmans et al., *J. Clin. Microbiol.* 29:2685–2689 (1991), Scieux et al., *Res. Microbiol.* 143:755–765 (1992), and Holland et al., *Infect. Immun.*, supra, describe the use of probes directed to *C. trachomatis* rRNA. Cheema et al., *Amer. J. Med. Sci.* 302:261–268 (1991) describe probes directed to Chlamydia ribosomal DNA. Pollard et al., *Mol. Cell. Probes* 3:383–389 (1989), Roosendaal, supra, and Claas et al., *Eur. J. Clin. Microbiol Infec. Dis.* 9:864–868 (1990) describe the amplification of nucleotide sequences derived from the 16S ribosomal subunit of Chlamydia species.

SUMMARY OF THE INVENTION

The featured invention discloses and claims amplification oligonucleotides, helper oligonucleotides, and oligonucleotide hybridization assay probes which are designed to be complementary to specific regions of *C. trachomatis* rRNA or the DNA encoding it, or to an oligonucleotide or nucleic acid having, consisting essentially of, or consisting of a *C. trachomatis* rRNA or rDNA nucleotide sequence.

The hybridization probes of the present invention are designed to hybridize to a target nucleic acid in a region of the molecule having a specific target nucleotide sequence under conditions which allow the selective detection of the target nucleic acid.

The amplification oligonucleotides of the present invention are designed and/or selected to hybridize to a region of a target nucleic acid which lies to the 3' side of a target nucleotide sequence (with respect to the target nucleic acid). The hybridized amplification oligonucleotide therefore permits the synthesis of a nucleic acid strand complementary to at least a portion of the target nucleic acid. The nacent strand also contains the target nucleotide sequence. The amplification oligonucleotides may or may not have as high a degree of specificity for the target nucleic acid as the hybridization assay probes disclosed herein. For example, amplification oligonucleotides may not be species-specific, but may be genus or family specific. However, as long as the amplification products (amplicons) are detected with a species-specific hybridization assay probe, the lack of absolute specificity will not defeat the utility of the amplification oligonucleotides in the detection of *C. trachomatis*.

Thus, a basic and novel characteristic of the amplification oligonucleotides, helper oligonucleotides and hybridization probes of the present invention is their ability, under appropriate hybridization reaction conditions, to preferentially hybridize to a predetermined region of a target *C. trachomatis* nucleic acid over non-targeted nucleic acids or nucleic acid regions. This specificity is a function of the degree of complementarity between the nucleotide sequences of the regions of the target nucleic acid and amplification oligonucleotide or hybridization probe involved in the hydrogen-bonded hybridization complex, as well as the hybridization reaction conditions. The present invention also discloses and claims double-stranded nucleic acid hybrid molecules formed between the hybridization probes or amplification oligonucleotides and their specific target nucleic acids. Hybrids formed between labeled probes and target nucleic acid molecules are useful for the detection and/or quantification of *C. trachomatis*, since these structures may be physically or chemically distinguished from unhybridized labeled probe after the hybridization reaction and the label thereon is thus the sole indication of the presence of the target nucleic acid in the original sample.

Similarly, the hybrids of the present invention formed between amplification oligonucleotides and their target nucleic acid sequence regions provide an initiation site for at least one round of DNA synthesis, RNA transcription, or both. The resulting amplified nucleic acid sequence region is then detected using a hybridization assay probe to form a detectable hybrid molecule, as explained more fully in the following text. Thus, both types of hybrid molecule are useful to obtaining objects of the present invention.

Therefore it is one object of the present invention to provide amplification oligonucleotides capable of amplifying a *C. trachomatis* target nucleotide sequence. A *C. trachomatis* target nucleotide sequence is a nucleotide sequence present in DNA or RNA contained within *C. trachomatis*, preferably *C. trachomatis* nucleic acid, and the nucleotide sequence perfectly complementary thereto. Preferably, the nucleic acid sequence regions to which the amplification oligonucleotides bind are not present in closely related bacterial species. However, neither amplification oligonucleotides nor helper oligonucleotides need be species specific to allow amplification of *C. trachomatis* nucleic acids or to assist in the binding of hybridization assay probes which are themselves specific for the detection of *C. trachomatis*.

Thus, it is another object of the present invention to disclose oligonucleotide hybridization assay probes capable of distinguishing *C. trachomatis* from other microorganisms in a test sample. These probes have a high degree of specificity for *C. trachomatis* nucleic acids, and will hybridize thereto under hybridization conditions which do not favor hybridization of the same probe to nucleic acids from closely related organisms such as *C. pneumoniae* or *C. psittaci*. Thus, the use of labeled probes allows the specific detection or quantification of *C. trachomatis* in a test sample containing these organisms. These probes may be used alone in a hybridization assay, or may be used in conjunction with helper oligonucleotides. The hybridization assay probes may be used directly to detect unamplified target nucleic acids, or may be used to detect nucleic acids having *C. trachomatis* nucleotide sequences obtained via nucleic acid amplification.

It is another object of the present invention to allow for the rapid, specific, and reproducible identification of *C. trachomatis* in a test sample derived from a cervical or urethral swab or other sample by the use of hybridization assay probes and helper oligonucleotides directed to *C. trachomatis* nucleic acids.

It is another object of the present application to increase the sensitivity of a nucleic acid hybridization assay by increasing the number of nucleic acid molecules having a *C. trachomatis* target nucleotide sequence in a test sample.

It is another object of the present invention to provide a composition to increase the hybridization rate of a *C. trachomatis*-specific hybridization assay probe to its target nucleic acid, as well as to increase the stability of the hybrid thereby formed by using helper oligonucleotides capable of hybridizing to *C. trachomatis* nucleic acids, thereby facilitating the binding of the labeled probe to its target.

DESCRIPTION OF THE PREFERRED EMBODIMENTS AND BEST MODE

Definitions

The following terms have the indicated meanings in the specification unless expressly indicated otherwise.

By "target nucleic acid" is meant a single- or double-stranded nucleic acid having a target nucleotide sequence.

By "oligonucleotide" is meant a single-stranded nucleotide polymer of greater than 2 nucleotides in length, preferably between 10 and 100 nucleotides, most preferably between 12 and 50 nucleotides in length. Such oligonucleotides may be joined by phosphodiester linkages, by phosphorothioate linkages, or by other rare or non-naturally-occurring linkages. Furthermore, an oligonucleotide may have uncommon nucleotides or non-nucleotide moieties. An oligonucleotide as defined herein is a nucleic acid, preferably DNA, but may be RNA or have a combination of ribo- and deoxyribonucleotides covalently linked. Oligonucleotide probes and amplification oligonucleotides of a defined sequence may be produced by techniques known to those of ordinary skill in the art, such as by chemical or biochemical synthesis, and by in vitro or in vivo expression from recombinant nucleic acid molecules, e.g., bacterial or retroviral vectors. As intended by this disclosure, an oligonucleotide does not consist of chromosomal DNA or the in vivo transcription products thereof.

By "target nucleic acid sequence", "target nucleotide sequence" or "target sequence" is meant a specific desired deoxyribonucleotide or ribonucleotide sequence comprising all or a part of the nucleotide sequence of a single-stranded target nucleic acid molecule, and the deoxyribonucleotide or ribonucleotide sequence perfectly complementary thereto.

A "substantially similar" nucleotide sequence is a nucleotide sequence identical to, or having no more than 20% mismatches, deletions and/or additions (excluding RNA or DNA equivalent nucleotides) as compared to a particular nucleic acid sequence. A substantially similar nucleotide sequence will have no more than 8 additional nucleotides complementary to the target nucleic acid, and will have no more than 4 less nucleotides than the reference nucleotide sequence. In addition, an oligonucleotide having a substantially similar nucleotide sequence can form a stable hybrid with a nucleic acid having a perfectly complementary nucleotide sequence to the particular nucleic acid sequence under stringent hybridization conditions.

"Stringent" hybridization assay conditions refer to conditions wherein a specific hybridization assay probe is able to hybridize with target nucleic acids (preferably rRNA or rDNA of *C. trachomatis*) and not significantly with other nucleic acids present in the test sample derived either from other microorganisms (e.g., *Chlamydia pneumoniae* and *Chlamydia psittaci*) or from humans. It will be appreciated that these conditions may vary depending upon factors including the GC content and length of the probe, the hybridization temperature, the composition of the hybridization reagent or solution, and the degree of hybridization specificity sought. Examples of specific stringent hybridization conditions are provided in the disclosure below.

By "probe" is meant a single-stranded oligonucleotide having a sequence partly or completely complementary to a nucleic acid sequence sought to be detected, so as to stably hybridize thereto under stringent hybridization conditions. In the case of a group or species-specific probe, the probe has the ability to stably hybridize to a target nucleic acid and not to non-target nucleic acids such as those from organisms outside the phylogenetic group or species under stringent hybridization conditions. Probes may, but need not, have regions which are not complementary to a target sequence, as long as such sequences do not substantially alter the probe's desired specificity under stringent hybridization conditions. If such non-complementary regions exist they may contain a 5' promoter sequence and/or a binding site for RNA transcription, a restriction endonuclease recognition site, or may contain sequences which will confer a desired secondary or tertiary structure, such as a catalytic active site or a hairpin structure on the probe, on the target nucleic acid, or both. A probe may be labeled with a reporter group moiety such as a radioisotope, a fluorescent or chemiluminescent moiety, with an enzyme or other ligand, which can be used for detection or confirmation that the probe has hybridized to the target sequence. One use of a probe is as a hybridization assay probe; probes may also be used as in vivo or in vitro therapeutic oligonucleotides or antisense agents to block or inhibit gene transcription, mRNA splicing, or translation in diseased, infected, or pathogenic cells.

As used in this disclosure, the phrase "a probe (or oligonucleotide) having a nucleic acid sequence consisting essentially of a sequence selected from" a group of specific sequences means that the probe, as a basic and novel characteristic, will form a stable hybrid with a nucleic acid in a nucleotide sequence region having a nucleotide sequence exactly complementary to one of the listed nucleic acid sequences of the group under stringent hybridization conditions. An exact complement under this definition includes the corresponding DNA or RNA sequence.

By "nucleic acid hybrid" or "hybrid" is meant a nucleic acid structure containing a double-stranded, hydrogen-bonded region, preferably of between 10 and 100 nucleotides in length, most preferably of between about 12 and 50 nucleotides in length, wherein each strand is complementary to the other and wherein the region is sufficiently stable under stringent hybridization conditions to be detected by means including but not limited to chemiluminescent or fluorescent light detection, autoradiography, or gel electrophoresis. Such hybrids may comprise RNA:RNA, RNA:DNA, or DNA:DNA duplex molecules.

By "complementary" is meant that the nucleotide sequences of similar regions of two single-stranded nucleic acids, or to different regions of the same single-stranded nucleic acid have a nucleotide base composition that allows the single strands to hybridize together in a stable double-stranded hydrogen-bonded region under stringent hybridization conditions. When a contiguous sequence of nucleotides of one single stranded region is able to form a series of "canonical" hydrogen-bonded base pairs with an analogous sequence of nucleotides of the other single-stranded region such that A is paired with U or T, and C is paired witch G, the nucleotides sequences are "perfectly" complementary.

By "conservatively modified variants" is meant nucleic acids or oligonucleotides having a nucleotide sequence that is complementary to a first nucleotide sequence region of a first nucleic acid, wherein the first nucleotide sequence region is perfectly complementary to a second nucleotide sequence region contained in a second "reference" nucleic acid. Conservatively modified variants have no more than 4 additional nucleotides and no more than 4 less nucleotides than the reference nucleic acid. It will be understood that such conservatively modified variants may have 5' non-complementary nucleotides which are more than 4 nucleotides longer than the reference nucleotide sequence. Conservatively modified variants will form a stable hybrid with a target nucleic acid region having a *C. trachomatis* nucleotide sequence under stringent hybridization conditions.

By "amplification oligonucleotide" is meant an oligonucleotide capable of hybridizing to a target nucleotide sequence region thereby acting as a primer for nucleic acid synthesis or a promoter template (e.g., for synthesis of a complementary strand, thereby forming a functional promoter sequence) for the initiation of RNA synthesis, or both. If the amplification oligonucleotide is designed to initiate RNA synthesis, the oligonucleotide may have nucleotide sequence regions which are non-complementary to the target nucleic acid, but which are recognized by an RNA polymerase (such as T7, T3 and SP6 RNA polymerase). An amplification oligonucleotide may or may not have a 3' terminus which is blocked to prevent or lessen the amount of primer extension. An amplification oligonucleotide as defined herein will preferably be between 12 and 100 nucleotides in length; more preferably between about 15 and 50 nucleotides in length.

By "nucleic acid amplification" or "target amplification" is meant increasing the number of nucleic acid molecules having at least one target nucleic acid sequence.

By "antisense" or "negative sense" is meant having a nucleic sequence complementary or substantially complementary to that of a reference nucleic acid sequence.

By "sense", "same-sense" or "positive sense" is meant having a nucleic acid sequence identical or substantially identical to that of a reference nucleic acid sequence.

By "helper oligonucleotide" is meant a normally unlabeled nucleic acid probe designed to hybridize with the target nucleic acid at a different locus than that of a labeled hybridization assay probe, thereby either increasing the rate of hybridization of the labeled probe, increasing the melting temperature ($T_m$) of the target:labeled probe hybrid, or both.

DETAILED DESCRIPTION OF THE INVENTION

The present invention is directed to amplification oligonucleotides, helper oligonucleotides and hybridization assay probes to be used for the specific detection of *C. trachomatis* nucleic acids. All of the oligonucleotides disclosed and claimed herein share in common the fact that they contain at least one nucleotide sequence region complementary to that of a *C. trachomatis* nucleic acid.

Hybridization Conditions and Probe/Primer Design

Hybridization reaction conditions, most importantly the temperature of hybridization and the concentration of salt in the hybridization solution, can be selected to allow the amplification oligonucleotides or hybridization probes of the present invention to preferentially hybridize to nucleic acids having a target *C. trachomatis* nucleotide sequence over other, untargeted nucleic acids suspected of being present in the test sample. At decreased salt concentrations and/or increased temperatures (called increased stringency) the extent of nucleic acid hybridization decreases as hydrogen bonding between paired nucleotide bases in the double-stranded hybrid molecule is disrupted; this process is called "melting".

Generally speaking, the most stable hybrids are those having the largest number of contiguous perfectly matched (i.e., hydrogen-bonded) nucleotide base pairs. Thus, such hybrids would usually be expected to be the last to melt as the stringency of the hybridization conditions increases. However, a double-stranded nucleic acid region containing one or more mismatched, "non-canonical", or imperfect base pair (resulting in weaker or non-existent base pairing at that position in the nucleotide sequence of a nucleic acid) may still be sufficiently stable under conditions of relatively high stringency to allow the nucleic acid hybrid to be detected in a hybridization assay without cross reacting with other, non-targeted nucleic acids present in the test sample.

Hence, depending both upon the degree of sequence variation between nucleic acids of the target organism and those of non-target but closely-related organisms on one hand, and the degree of complementarity between the nucleotide sequence of a particular amplification oligonucleotide or hybridization probe and that of the target nucleic acid on the other, one or more mismatches between the probe and the target will not necessarily defeat the ability of the oligonucleotide to hybridize to target over non-target nucleic acids.

The hybridization assay probes of the present invention were chosen, selected, and/or designed to maximize the difference between the melting temperatures of the probe::target hybrid ($T_m$, defined as the temperature at which half of the potentially double-stranded molecules in a given reaction mixture are in a single-stranded, denatured state) and the $T_m$ of a mismatched hybrid formed between the probe and the rRNA or rDNA of the phylogenetically most closely-related organisms expected to be present in the test sample, but not sought to be detected. While the unlabeled amplification oligonucleotides and helper oligonucleotides need not have such an extremely high degree of specificity as the labeled hybridization assay probe to be useful in the present invention, they are generally designed in a similar manner to preferentially hybridize to target nucleic acids of one or more organism over other nucleic acids.

Nucleotide sequences of the rRNA of *C. trachomatis* and closely related organisms such as *C. psittaci* and *C. pneumoniae* were obtained from published sources, or were independently determined by the Applicant using nucleic acid sequencing techniques well known in the art. See e.g., Lane et al., Proc. Natl. Acad. Sci. 82:6955 (1985).

By aligning the rRNA sequences of these various organisms, applicant has discovered specific discrete regions of relative interspecies variability. Those regions which displayed the greatest amount of nucleotide sequence variability between the target organism, *C. trachomatis*, and the "untargeted" organisms, e.g., *C. pneumoniae* and *C. psittaci*, were chosen as potential target regions for the design of species-specific hybridization assay probes.

Merely identifying putatively unique potential target nucleotide sequences does not guarantee that a functionally species-specific hybridization assay probe may be made to hybridize to *C. trachomatis* rRNA or rDNA comprising that sequence. Various other factors will determine the suitability of a nucleic acid locus as a target site for species-specific probes. By way of example: increasing the GC content of the potential target nucleotide sequence (and thus of the double-stranded probe:target hybrid) generally increases the stability and thus the $T_m$ of the hybrid. The number of contiguous nucleotides within that sequence region which are identical to one or more of the "untargeted" organisms also affect the stability, and thus the $T_m$, of a partially mismatched hybrid between a probe perfectly complementary to *C. trachomatis* rRNA, and a nucleic acid having rRNA nucleotide sequences of the untargeted organism or organisms. Thus, if the difference in the melting temperatures of the two hybrids is not sufficiently large, normally at least 2°–5° C., a probe may not be species specific despite being targeted to a unique region.

The desired temperature of hybridization and the hybridization solution composition (such as salt concentration) are the two conditions having the major effect on the stability of double-stranded hybrids; these conditions must be taken into account in constructing a group- or species-specific probe. The thermal stability of hybrid nucleic acids increases with the ionic strength of the reaction mixture. On the other hand, chemical reagents which disrupt hydrogen bonds, such as formamide, urea, dimethyl sulfoxide and alcohols, can greatly reduce the thermal stability of the hybrids.

To maximize the specificity of a probe for its target, the subject probes of the present invention were designed to hybridize with their targets under conditions of high stringency. Under such conditions only single nucleic acid strands having a high degree of complementarity will hybridize to each other; single nucleic acid strands without such a high degree of complementarity will tend not to form hybrids. Accordingly, the stringency of the assay conditions (i.e., the temperature and the ionic strength) can determine the amount of complementarity which should exist between two nucleic acid strands in order to form a hybrid. In conjunction with the present invention, stringency is chosen to maximize the difference in stability between the hybrid formed between the probe and the target nucleic acid and potential hybrids formed between the probe and any single stranded non-target nucleic acids present.

Proper probe specificity may be designed by minimizing of the length of the probe having a nucleotide sequence perfectly complementary to sequences of non-target organisms, by avoiding G and C rich regions of homology to non-target sequences, and by constructing the probe to contain as many destabilizing mismatches to nontarget sequences as possible.

The length of the target nucleic acid sequence, and accordingly the total length of the probe sequence, can also be important to specificity. In some cases, there may be several nucleotide sequences in a particular "variable" region, differing in location and length, which may be used as species-specific probe targets. In some cases a species-specific probe cannot be designed to a particular rRNA variable region, either because the sequence region is not accessable to the probe, or for other reasons. While it is possible for nucleic acids that are not perfectly complementary to hybridize, the longest stretch of perfectly homologous base sequence will generally determine hybrid stability. Oligonucleotide probes of different lengths and base composition may be used.

Target regions which form strong intramolecular structures inhibitory to hybridization are less preferred target regions. Likewise, probe designs which result in extensive self-complementarity should be avoided. As explained above, hybridization is the association of two single strands of complementary nucleic acids to form a hydrogen-bonded double-stranded hybrid. Thus, if one or both of the two strands is wholly or partially involved in intramolecular or intermolecular bonding it will be less able to participate in the formation of a new intermolecular probe:target hybrid. Ribosomal RNA molecules, for example, are known to form very stable intramolecular helices and secondary structures by hydrogen bonding. By designing a hybridization assay so that a substantial portion of the targeted sequence remains in a single-stranded state until hybridization with the probe, the rate and extent of hybridization between probe and target may be greatly increased. One way this may be accomplished is by choosing as a target nucleotide sequence a sequence that is relatively uninvolved in intramolecular hydrogen-bonding. Alternatively or additionally, the hybridization assay probe may be used in a probe mix with helper oligonucleotides which can make the target site more accessible for hybridization with the hybridization assay probe. Such helper probes are generally described.

A number of formulae are available which provide an estimate of the melting temperature for perfectly matched oligonucleotides to their target nucleic acids. One such formula, $$T_m = 81.5 + 16.6(log_{10}[Na^+]) + 0.41(\text{fraction } G+C) - (600/N)$$

(where N=the length of the oligonucleotide in number of nucleotides) provides a good estimate for the $T_m$ for oligonucleotides between about 14 and 70 nucleotides in length. From such calculations, subsequent empirical verification or "fine tuning" of the $T_m$ may be made using screening techniques. (For further information on hybridization and oligonucleotide probes see e.g., Sambrook et al., *Molecular Cloning: A Laboratory Manual* (Cold Spring Harbor Laboratory Press 1989) hereby incorporated by reference herein (at Chapter 11). This reference, also provides estimates of the effect of mismatches on the $T_m$ of a hybrid.

Nucleic Acid Amplification

Preferably, the amplification oligonucleotides of the present invention are oligodeoxynucleotides and are sufficiently long to be used as a template for the synthesis of specific primer extension products by a nucleic acid polymerase. As is true for the design of probes, optimal primer length should take into account several factors, including the temperature of reaction, the structure and base composition of the primer, and how the primer is to be used. For example, for optimal specificity the oligonucleotide primer generally should contain at least about 12 nucleotides, depending on the complexity of the target nucleic acid sequence. If such specificity is not essential, shorter primers may be used; in such a case, it may be desirable to carry out reaction at lower temperatures in order to form stable hybrid complexes with the template nucleic acid.

A nucleic acid polymerase used in conjunction with the amplification oligonucleotides of the present invention refers to a chemical, physical or biological agent which incorporates either ribo- or deoxyribonucleotides, or both, into a covalently-linked nucleic acid polymer, or strand, in a template-dependent manner. Examples of nucleic acid polymerases are enzymes having DNA-directed DNA polymerase, RNA-directed DNA polymerase, and/or RNA polymerase activities. DNA polymerases bring about nucleic acid synthesis in a template-dependent manner and in a 5' to 3' direction. Because of the antiparallel orientation of the two strands in a double-stranded nucleic acid, this direction is from a 3' region on the template to a 5' region on the template. Examples of DNA-directed DNA polymerases include *E. coli* DNA polymerase I, the thermostable DNA polymerase from *Thermus aquaticus* (Taq), and the thermostable DNA polymerase from *Bacillus stearothermophilus* (Bst). Examples of RNA directed DNA polymerases include various retroviral reverse transcriptases, such as MMLV reverse transcriptase or AMV reverse transcriptase.

During most nucleic acid amplification reactions, a nucleic acid polymerase adds nucleotide residues to the 3' end of the primer using the target nucleic acid as a template, thus synthesizing a second nucleic acid strand having a nucleotide sequence partially or completely complementary to a region of the target nucleic acid. In many nucleic acid amplification reactions, the two strands comprising the resulting double-stranded structure must be separated by chemical or physical means in order to allow the amplification reaction to proceed. Alternatively, the newly-synthesized template strand may be made available for hybridization with a second primer or promoter-primer through the use of a nucleolytic enzyme which digests part or all of the original target strand without digesting the newly synthesized strand. In this way the process may be repeated through a number of cycles, resulting in a large increase in the number of nucleic acid molecules having the target nucleotide sequence.

Either the first or second amplification oligonucleotide, or both, may be a promoter-primer. Such a promoter-primer usually contains nucleotide sequences that are not complementary to those of the target nucleic acid molecule, or primer extension product(s). These non-complementary sequences may be located 5' to the complementary sequences on the amplification oligonucleotide, and may provide a locus for initiation of RNA synthesis when made double-stranded through the action of a nucleic acid polymerase. The promoter thus provided may allow for the in vitro transcription of multiple RNA copies of the target nucleic acid sequence. It will be appreciated that when reference is made to a primer in this specification, such reference is intended to include the primer aspect of a promoter-primer as well unless the context of the reference clearly indicates otherwise.

In some amplification systems, for example the amplification method of Dattagupta et al., supra, the amplification oligonucleotides may contain 5' non-complementary nucleotides which assist in strand displacement. Furthermore, when used in conjunction with a nucleic acid polymerase having 5' exonuclease activity, the amplification oligonucleotides may have modifications at their 5' end to prevent enzymatic digestion. Alternatively, the nucleic acid polymerase may be modified to remove the 5' exonuclease activity, such as by treatment with a protease that generates an active polymerase fragment without the 5' nuclease domain. In such a case the oligonucleotides need not be modified at their 5' end.

Preparation of Oligonucleotides

An oligonucleotide is made of nucleotide subunits covalently joined together. The sugar groups of the nucleotide subunits may be ribose, deoxyribose, or modified derivatives thereof such as O-methyl ribose. The nucleotide subunits may by joined by linkages such as phosphodiester linkages, modified linkages, or by non-nucleotide moieties that do not prevent hybridization of the oligonucleotide. Modified linkages include those linkages in which a standard phosphodiester linkage is replaced with a different linkage, such as a phosphorothioate linkage, or methylphosphonate linkage. As mentioned above, when used as a hybridization assay probe the oligonucleotide preferably contains a reporter group such as acridinium ester or a radioisotope to help identify hybridization of the probe to its target sequence.

All of the amplification oligonucleotides of the present invention can be readily prepared by methods known in the art. Preferably, the primers are synthesized using solid phase methods. For example, Carruthers, et al., describe using standard phosphoramidite solid phase chemistry to join nucleotides by phosphodiester linkages. (*Methods in Enzymology*, Volume 143, pg. 287 (1987)). Likewise, Bhatt describes a procedure for synthesizing oligonucleotides containing phosphorothioate linkages. (Bhatt, U.S. Pat. No. 5,252,723 which enjoys common ownership with the present invention.) Also, Klem et al., PCT Application No. WO 92/07864, describe the synthesis of oligonucleotides having different linkages including methylphosphonate linkages. The latter three references are hereby incorporated by reference herein. In addition, methods for the organic synthesis of oligonucleotides are known to those of skill in the art, and are described in Sambrook, et al., supra, previously incorporated by reference herein.

All the oligonucleotides of the present invention, whether hybridization assay probes, amplification oligonucleotides, or helper oligonucleotides, may be modified with chemical groups to enhance their performance or to facilitate the characterization of amplification products. For example, backbone-modified oligonucleotides such as those having phosphorothioate or methylphosphonate groups which render the oligonucleotides resistant to the nucleolytic activity of certain polymerases allow the use of such enzymes in an amplification or other reaction. Another example of modification involves using non-nucleotide linkers (e.g., Arnold, et al., European Patent Application 88308766-0, hereby incorporated by reference herein) incorporated between nucleotides or at an end of the oligonucleotide chain which do not prevent hybridization or the elongation of the primer. Amplification oligonucleotides may also contain mixtures of the desired modified and natural nucleotides, and may contain mixtures of ribo- and deoxyribonucleotides.

The 3' end of an amplification oligonucleotide may be blocked to reduce or prevent initiation of DNA synthesis as described by McDonough, et al., U.S. patent application No. 07/925,405 which enjoys common ownership with the present invention and is hereby incorporated by reference herein. A mixture of different 3' blocked promoter-primers, or of 3' blocked and unblocked promoter-primers may increase the efficiency of nucleic acid amplification, as described therein.

As disclosed above, the 5' end of the oligonucleotides may be modified to be resistant to the 5'-exonuclease activity present in some nucleic acid polymerases. Such modifications can be carried out by adding a non-nucleotide group to the terminal 5' nucleotide of the primer using techniques such as those described by Arnold, et al., supra, entitled "Non-Nucleotide Linking Reagents for Nucleotide Probes", previously incorporated by reference herein.

Amplification of *C. trachomatis* rRNA and rDNA

The amplification oligonucleotides of the present invention are directed to particular *C. trachomatis* 23S or 16S rRNA nucleotide sequences or their rDNA counterparts, and cause the amplification of at least one *C. trachomatis*-specific target nucleotide sequence region. The amplification oligonucleotides described herein comprise two sets of amplification oligonucleotides. Members of the first set of amplification oligonucleotides will hybridize with rRNA or rDNA regions having one of the following nucleotide sequences (or RNA versions of such sequences having uracil substituted for thymine).

23S rRNA-Specific

SEQ ID NO 12: GCGATCAAGG GGAATCTTCG GG,
SEQ ID NO 13: TCCAATCGTC CGCGTGCTTA ACTTACTCCG,
SEQ ID NO 14: TCTTCCAATC GTCCGCGTGC TTAACTTACT CCG,
SEQ ID NO 15: CTCAACACCT GAGTAGGACT AGAC,
SEQ ID NO 16: ATACATCCAT CTTTCCAGAT GTGTTCAACT AGG,

16S rRNA-Specific

SEQ ID NO 45: TTCCAACCGT TATTCCCAAG TTAAG-GACA

SEQ ID NO 51: TATCAGCTAG TTGGTGGGGT AAAG-GCC

Preferred embodiments of these amplification oligonucleotides have or consist essentially of the following sequences:

23S rRNA-Specific

SEQ ID NO 4: CCCGAAGATT CCCCTTGATC GC,

SEQ ID NO 5: CGGAGTAAGT TAAGCACGCG GAC-GATTGGA,

SEQ ID NO 6: CGGAGTAAGT TAAGCACGCG GAC-GATTGGA AGA,

SEQ ID NO 7: GTCTAGTCCT ACTCAGGTGT TGAG, and

SEQ ID NO 8: CCTAGTTGAA CACATCTGGAAAGATG-GATG TAT,

16S rRNA-Specific

SEQ ID NO 44: TGTCCTTAAC TTGGGAATAA CGTTG-GAA

SEQ ID NO 50: GGCCTTTACC CCACCAACTA GCT-GATA or RNA versions of these sequences, having uracil substituted for thymine. These oligonucleotides may also have additional, non-complementary bases at their 5' end comprising a promoter sequence able to bind an RNA polymerase and direct RNA transcription using the target nucleic acid as a template.

Preferably, the amplification oligonucleotides targeted to the nucleic acid region having sequence SEQ. ID. NO: 12 are used in combination with those targeted to regions of SEQ. ID. NOs: 13 and/or 14, the amplification oligonucleotides targeted to the nucleic acid region having sequence SEQ. ID. NO: 15 are used in combination with those targeted to the nucleic acid region having sequence SEQ. ID. NO: 16, and the amplification oligonucleotides targeted to the nucleic acid region having SEQ. ID. NO. 45 are used in combination with those targeted to the nucleic acid region having SEQ ID NO: 51. Thus, in a preferred embodiment amplification oligonucleotides of SEQ. ID. NO: 4 are used with those of SEQ. ID. NO: 5 and/or 6, amplification oligonucleotides of SEQ. ID. NO: 7 are used with those of SEQ. ID. NO: 8, and amplification oligonucleotides of SEQ ID NO: 44 are used with those of SEQ ID NO: 50.

Amplification oligonucleotides comprising the second set are directed to particular *C. trachomatis* 23S rRNA nucleotide sequences, or their rDNA counterparts, flanking at least one target nucleotide sequence region. These amplification oligonucleotides may be used in the same manner as the amplification oligonucleotides of the first set; for example, as members of a primer pair, of groups of nested primer pairs, or as an RNA polymerase initiation site. However, they differ from the members of the first set in the manner of their preferred use in an isothermal strand displacement nucleic acid amplification system, as described in detail below. These oligonucleotides will hybridize with a nucleic acid having one of the following nucleotide sequences, or RNA versions of such sequences having uracil substituted for thymine.

SEQ ID NO: 30 5'-CAACACCTGA GTAGGACTAG ACGCG-3'

SEQ ID NO: 31 5'-CCTAGTCTGA ATCTGGGG-3'

SEQ ID NO: 32 5'-AAGGCTAAAT ACTAGTCAAT GACCG-3'

SEQ ID NO: 33 5'-AGTGAACCAG TACTATGAAG AAA-3'

SEQ ID NO: 34 5'-AACCCTTGTT AAGGGAGTGAAAT-3'

SEQ ID NO: 35 5'-ACCTGAAACC TGTAGCTTAC AA-3'

SEQ ID NO: 36 5'-GGTCGCAGAC CAATTGCCCG T-3'

SEQ ID NO: 37 5'-ATTCGGACCT CCGGGTCTTT GCT-3'

SEQ ID NO: 38 5'-TCGCTTTGCA TACCTATGTA TTC-3'

SEQ ID NO: 39 5'-ACTAAGATGT TTCAGTTCGG CAGG-3'

SEQ ID NO: 40 5'-ATCTCTTCGA TTTCTTTTCC TCTG-3'

SEQ ID NO: 41 5'-ATCCTTTATC CTCAATCCTA CA-3'

SEQ ID NO: 42 5'-TCTTTCCAGA TGTGTTCAAC TAG-GAGTCC-3'

Preferred embodiments of the oligonucleotides comprising the second set of amplification oligonucleotides have the following nucleotide sequences:

SEQ ID NO: 17 5'-CGCGTCTAGT CCTACTCAGG TGTTG-3',

SEQ ID NO: 18 5'-CCCCAGATTC AGACTAGG-3'

SEQ ID NO: 19 5'-CGGTCATTGA CTAGTATTTA GCCTT-3'

SEQ ID NO: 20 5'-TTTCTTCATA GTACTGGTTC ACT-3'

SEQ ID NO: 21 5'-ATTTCACTCC CTTAACAAGG GTT-3'

SEQ ID NO: 22 5'-TTGTAAGCTA CAGGTTTCAG GT-3'

SEQ ID NO: 23 5'-ACGGGCAATT GGTCTGCGAC C-3'

SEQ ID NO: 24 AGCAAAGACC CGGAGGTCCG AAT

SEQ ID NO: 25 GAATACATAG GTATGCAAAG CGA

SEQ ID NO: 26 CCTGCCGAAC TGAAACATCT TAGT

SEQ ID NO: 27 CAGAGGAAAA GAAATCGAAG AGAT

SEQ ID NO: 28 TGTAGGATTG AGGATAAAGG AT

SEQ ID NO: 29 GGACTCCTAG TTGAACACAT CTG-GAAAGA as well as RNA versions of these sequences having uracil substituted for thymine. In a most preferred embodiment, these oligonucleotides have additional non-complementary nucleotides at their 5' ends so as to further enhance displacement of the primer extension products.

All of the amplification oligonucleotides of the present invention may have nucleotide sequences containing no modifications, deletions, or additions to the sequences listed above. However, the amplification oligonucleotides may also or alternatively have modifications, such as blocked and/or modified 3' and/or 5' termini or additions including but not limited to the addition of a specific nucleotide sequence that is recognized by an RNA polymerase, (e.g., the promoter sequence for T7, T3, or SP6 RNA polymerase), addition of sequence regions which cause or enhance initiation or elongation of RNA transcription by an RNA polymerase, or sequence regions which may provide for intramolecular base pairing and encourage the formation of secondary or tertiary nucleic acid structures.

Amplification oligonucleotides are used in a nucleic acid amplification procedure, such as the polymerase chain reaction or an amplification reaction using RNA polymerase, DNA polymerase and RNAse H activities, as described by Kacian and Fultz, supra, Dattagupta et al., supra, and by Sninsky et al., U.S. Pat. No. 5,079,351; both hereby incorporated by reference herein, the first two of which enjoy common ownership with the present invention.

A wide variety of methods are available to detect an amplified target sequence. For example, the nucleotide substrates or the primers can include a detectable label which is incorporated into newly synthesized DNA. The resulting labelled amplification product can then be separated from the unused labelled nucleotides or primers and the label is detected in the separated product fraction.

Substances which can serve as useful detectable labels are well known in the art and include radioactive isotopes, fluorescent compounds, chemiluminescent compounds, chromophores, as well as ligands such as biotin and haptens which, while not directly detectable, can be readily detected by a reaction with labelled forms of their specific binding partners, e.g., avidin and antibodies, respectively.

Another approach is to detect the amplification product by hybridization with a detectable nucleic acid probe and measuring the resulting labeled hybrids in any conventional manner. In a preferred use, the product can be assayed by hybridizing a chemiluminescent acridinium ester-labelled nucleic acid probe to the target sequence, selectively hydrolyzing the acridinium ester present on unhybridized probe, and measuring the chemiluminescence produced from the remaining acridinium ester in a luminometer. See, e.g., Arnold, et al., supra, PCT Application No. US88/02746, Arnold and Nelson, U.S. Pat. No. 5,283,174, and Nelson, et al., "Non-Isotopic DNA Probe Technologies", Academic Press, San Diego (KRICKA, ed. 1992); these references are hereby incorporated by reference herein, and the former two references enjoys common ownership with the present invention.

Oligonucleotide Hybridization Assay Probes to *C. trachomatis* rRNA and rDNA

The oligonucleotide hybridization assay probes disclosed and claimed herein are able to preferentially hybridize to target nucleic acids containing *C. trachomatis* rRNA or rDNA nucleotide sequences over the nucleic acids of phylogenetically closely related bacterial species, preferably *C. psittaci* and *C. pneumoniae*. These hybridization assay probes were designed, selected and/or chosen based upon a comparision of the nucleotide sequences of corresponding regions of the ribosomal RNA of *C. trachomatis* and said phlogenetically closely-related species.

The hybridization assay probes of the present invention are complementary to the following target rDNA nucleotide sequences or RNA versions thereof, having uracil substituted for thymine:
SEQ ID NO: 9 CGTTCTCATC GCTCTACGGA CTCT,
SEQ ID NO: 10 CGGTCTTTCT CTCCTTTCGT CTACGGG,
SEQ ID NO: 46 CCGAATGTGG CGATATTTGG GCATCC, or the nucleotide sequences perfectly complementary thereto.

Preferred embodiments of these oligonucleotide hybridization assay probes have the nucleotide sequence:
SEQ ID NO: 1 AGAGTCCGTA GAGCGATGAG AACG,
SEQ ID NO: 3 CCCGTAGACG AAAGGAGAGAAA-GACCG,
SEQ ID NO: 47 GGATGCCCAAATATCGCCAC ATTCGG, and RNA versions thereof, having uracil substituted for thymine.

The oligonucleotide hybridization assay probes of the present invention are preferably labeled with a detectable label such as a radioisotope, a fluorescent or chemiluminescent moiety, with an enzyme or other ligand, which can be used for detection or confirmation that the probe has hybridized to the target sequence. The Applicant prefers the use of chemiluminescent acridinium esters as labels. See Arnold et al., U.S. Pat. No. 5,185,439, which enjoys common ownership with the present application and is incorporated by reference herein. The assay probe is mixed with a sample suspected of containing a nucleic acid having the target sequence under hybridization conditions suitable for allowing annealing of the two strands by hydrogen bonding in the region of complementarity. The probe may also be combined with one or more unlabeled helper oligonucelotide to facilitate binding to the nucleic acid having the target *Chlamydia trachomatis* nucleotide sequence. The probe then hybridizes to the target nucleic acid present in the sample; the resulting hybrid duplex may be separated and detected by various techniques well known in the art, such as hydroxyapatite adsorption and radioactive monitoring. Also included among these techniques are those that involve selectively degrading the label present on unhybridized probe and then measuring the amount of label associated with the remaining hybridized probe, as disclosed in Arnold et al., U.S. Pat. No. 5,283,174, which enjoys common ownership with the present application and is incorporated by reference herein. This latter technique, is presently preferred by the Applicants.

Helper Oligonucleotides used in the Detection of *C. trachomatis*

Specific helper oligonucleotides were used to facilitate the hybridization of the hybridization assay probes to the target nucleic acid. Helper oligonucleotides are described in Hogan and Milliman, U.S. Pat. No. 5,030,557, which enjoys common ownership with the present application and is hereby incorporated by reference herein. Specific helper oligonucleotides for facilitating the specific detection of *C. trachomatis* have nucleotide sequences complementary to a *C. trachomatis* nucleotide sequence of:
SEQ ID NO: 11 CCTGATCTTA TGTTAGCGGA TTTGC-CTACT AAC,
SEQ ID NO: 49 CCTAAGATCC CCTTCTTTAA CGT-TACTC, and RNA versions thereof, having uracil substituted for thymine.

A preferred embodiment of this helper oligonucleotide is an oligonucleotide having the nucleotide sequence of:
SEQ ID NO: 2 GTTAGTAGGC AAATCCGCTA ACATAA-GATC AGG,
SEQ ID NO: 48 GAGTAACGTT AAAGAAGGGG ATCT-TAGG.

Helper oligonucleotides generally may be used under stringent hybridization conditions, but are not necessarily species specific in their selectivity; i.e., the target nucleotide sequences for the helper oligonucleotides are not necessarily unique to the species *C. trachomatis*.

Preferably, hybridization assay probes are used in combination with amplification oligonucleotides and may be used with helper oligonucleotides for the detection of *C. trachomatis*. In preferred combinations, the oligonucleotides of the present invention having the indicated nucleotide sequences are used in the following combinations for the detection of *C. trachomatis*.

|  | Hybridization Assay Probe | Amplification Oligonucleotide | Helper Oligonucleotide |
|---|---|---|---|
| Combination 1 | SEQ ID NO: 1 | SEQ ID NO: 4 and SEQ ID NO: 5 or SEQ ID NO: 6 | SEQ ID NO: 2 |
| Combination 2 | SEQ ID NO: 3 | SEQ ID NO: 7 and SEQ ID NO: 8 | |
| Combination 3 | SEQ ID NO: 46 | SEQ ID NO: 44 and SEQ ID NO: 50 | SEQ ID NO: 48 |

Preferred Method of Use for Amplification Oligonucleotides Used in Primer Array for Amplification of *C. trachomatis*

While all of the amplification oligonucleotides of the present invention may be used in conjunction with many nucleic acid amplification methods for the amplification of *C. trachomatis* nucleic acids, such as those methods described above and disclosed in the examples which follow, in a preferred embodiment those amplification oligonucleotides targeted to nucleic acids having ribosomal nucleotide sequences SEQ ID NO: 30 through 42 are used together in a primer array, as disclosed in Dattagupta, et al., supra, which enjoys common ownership with the present application and is hereby incorporated by reference as part of this disclosure. According to the amplification method disclosed therein, an array of primers can be used to amplify a single target nucleic acid sequence without the need for thermocycling or degradation of one of the two strands after each primer extension reaction.

In a preferred use, amplification oligonucleotides having the sequences SEQ ID NO: 17 through 29 comprise a primer array for use in conjunction with a DNA polymerase lacking 5' to 3' exonucleolytic activity. The primer array is made up of a first subset of primers (having SEQ. ID. NO: 17–23) with nucleotide sequences complementary to the initial target nucleic acid (*C. trachomatis* rRNA or rDNA) and a second subset of primers (having SEQ. ID. NO: 24–29) each having a nucleotide sequence of the same sense of a region of the *C. trachomatis* target rRNA or rDNA. These two subsets of primers will be referred to as complementary primers and sense primers, respectively. Each primer's nucleotide sequence need not reflect the exact sequence of the template but must be able to form a stable hybrid with a template strand under defined amplification conditions. Each newly-formed primer extension product, once displaced, can itself act as a template for additional nucleic acid synthesis. Moreover, the amplification reaction can occur under constant temperature and reaction conditions so long as the nucleic acid polymerase used in the method is active at the temperature of hybridization and strand displacement.

When the amplification oligonucleotides of this primer array are used in the preferred method of Dattagupta et al., supra, each member of the complementary subset of primers will hybridize to a predetermined locus of the target *C. trachomatis* nucleic acid such that the distance between hybridized complementary primers is preferably between one and two hundred nucleotides, most preferably between two and ten nucleotides. Upon addition of a nucleic acid polymerase (preferably a DNA polymerase) and nucleotide triphosphates (preferably deoxyribonucleotide triphosphates) under suitable reaction conditions, the addition of nucleotides to the 3' end of the oligonucleotides comprising the primer array may begin.

While not wishing to be bound by theory, it is Applicant's belief that this amplification reaction proceeds in the following manner. When a nascent nucleic acid strand extends to the position at which another primer originally hybridized (and from which a second nascent strand now extends), the newly-forming strand will often displace the second strand at the 5' terminus of the second strand, thus making the underlying target nucleic acid strand available as a template for further extension of the first nascent strand. Meanwhile, the second nascent strand will displace a third nascent strand as it extends, and so forth, resulting in as many nascent strands as there are complementary primers. All of these primers are designed to bind to the target nucleic acid on the 3' side (relative to the target nucleic acid) of the portion of the target nucleotide sequence desired to be amplified.

When the nascent strands have extended through and/or past the target nucleotide sequence, they will contain nucleotide sequences providing a hybridization substrate for the "sense primer" subset of the primer array. These primers are also designed in such a manner that primers of the same polarity are between one and two hundred nucleotides apart; more preferably the primers are separated by between one and ten nucleotides. It is Applicant's belief that these primers undergo the same sort of extension and strand displacement as do the complementary primers. The combined effect of the extension and strand displacement of the complementary and sense primer subsets results in a very rapid increase in the number of nucleic acids having the target nucleotide sequence in the reaction mixture.

The members of each primer set are used as initiation points for template-dependent synthesis of a nucleic acid strand, and are thought to enhance displacement of the synthesized strands resulting from elongation of neighboring primers of the same sense. Thus, strand displacement and nucleic acid synthesis are thought to be carried out in one step. This is a surprising finding, and Applicant is unclear of the exact mechanism by which the procedure operates.

While only two primers of a single sense are believed to be necessary to cause strand displacement during nucleic acid synthesis, a primer array comprising both complementary and sense primers is preferably used to amplify both the initial nucleic acid template and its complement in order to cause the exponential amplification of a nucleic acid bearing a target nucleic acid sequence.

Preferably, the nucleic acid polymerase used in this method lacks 5' exonuclease activity, and the procedure is performed at higher temperatures than those at which enzymes such as the Klenow fragment of *E. coli* DNA polymerase I operate; the reaction is more efficient at 43° C. than at 37° C. Thermostable DNA polymerases are known in the art (for example, Taq DNA polymerase and the DNA polymerase from *Bacillus stearothermophilus*); Klenow-type proteolytic fragments of these enzymes lacking the 5'-3' exonuclease activity have been made and reported. Optimal efficiency using this amplification method in conjunction with the amplification oligonucleotides of the present invention is obtained at temperatures between 50° C. and 70° C.

All of the amplification oligonucleotides exemplified by those having SEQ ID NOs 17 through 29 need not be used together in a primer array to amplify the target *C. trachomatis* nucleic acid, even using the preferred method. Preferably, at least two complementary primers and at least two sense primers selected from this primer array are used together in order to amplify the target sequence contained on the initial template nucleic acid and its complement. However, the degree of amplification has been found to increase with increasing numbers of primers. Preferably, the complementary primer set and the sense primer set each contain more than two primers. In most preferred embodiments, at least four sense primers and four complementary primers are used or at least seven sense primers and at least six complementary primers are used.

The following examples of various embodiments of the present invention are for illustration only, and are not intended to limit the scope of the invention.

Example 1:

In this experiment, differing amounts of purified *C. trachomatis* (ATCC No. VR-886) rRNA was amplified with two oligonucleotides of negative sense having a nucleotide sequence complementary to *C. trachomatis* 23S rRNA. Target 23S rRNA was obtained from *C. trachomatis* (See, Glisin et al., Biochemistry 13:2633 (1974)), and diluted in buffer (50 mM Tris-HCl (pH 8.3), 37.5 mM KCl, 1.5 mM MgCl$_2$, 10 mM DTT). Two promoter-primers were synthesized, each containing a T7 RNA polymerase promoter of nucleotide sequence of SEQ ID NO:43 covalently attached to the 5' end of a oligonucleotide of nucleotide sequence SEQ ID NO 4.

One of the promoter-primers was synthesized with a free 3'-terminal hydroxyl group, and was used at two pmol per reaction. The second promoter-primer was synthesized with an alkane diol group covalently bound to the 3' end to block or lessen the amount of primer extension, and was used at 13 pmol per reaction. The primers and varying amounts of the target nucleic acid and were heated to 95° C. for 15 minutes, cooled to 42° C. and 900 units of Moloney Murine Leukemia Virus (MMLV) reverse transcriptase and 400 units of T7 RNA polymerase were added to the solution. The final amplification mixture contained 50 mM Tris HCl (pH 8.5), 35 mM potassium chloride, 4 mM GTP, 4 mMATP, 4 mM UTP, 4 mM CTP, 1 mM dATP, 1 mM dTTP, 1 mM dCTP, 1 mM dGTP, 20 mM MgCl$_2$, 20 mM N-acetyl-L-cysteine, and 5% glycerol. After a two hour incubation at 42° C., amplification was assayed by hybridization of one hundred µl of the amplification reaction mixture with an acridinium ester-labeled probe having SEQ. ID. NO. 1 in a probe mixture containing an unlabeled helper probe having SEQ. ID. NO. 2. The hybridizations were performed in a solution containing 0.05M lithium succinate pH 5, 0.6M LiCl, 1% (w/v) lithium lauryl sulfate (LLS), 10 mM ethylene diamine tetraacetic acid (EDTA), 10 mM ethylene glycol bis (beta-amino ethyl ether) N,N,N',N' tetraacetic acid (EGTA) at 60° C. for 15 minutes. Three hundred microliters of a solution containing 0.15M sodium tetraborate pH 8.5, 1% TRITON® X-100 were added to each tube, and each reaction was incubated at 60° C. for 5–7 minutes, cooled to room temperature, and analyzed in a Gen-Probe LEADER® I luminometer (Gen-Probe Incorporated, San Diego, Calif.). The luminometer automatically injects two reagents, the first comprising 1 mM nitric acid and 0.1% hydrogen peroxide and the second comprising 1N sodium hydroxide. Assay results were given in Relative Light Units (RLU), a measure of the number of photons detected by the luminometer. Each reaction was performed in triplicate and the results are reported below.

Table 1: Amplification of *C. trachomatis* nucleic acid using amplification oligonucleotides having a target-binding nucleotide sequence of SEQ ID NO: 4, followed by detection with a hybridization assay probe of nucleotide sequence SEQ ID NO. 1.

TABLE 1

| Amount of Target | RLU |
| --- | --- |
| 1 × 10$^{-19}$ moles | 1,199,284 |
|  | 1,399,659 |
|  | 1,527,280 |
| 2 × 10$^{-20}$ | 1,383,200 |
|  | 1,077,035 |
|  | 874,951 |
| 0 moles | 1,858 |
|  | 1,824 |
|  | 1,734 |

These data indicate that the amplification of at least as little as 0.025 pg of *C. trachomatis* nucleic acid is successful, and can be detected in a nucleic acid hybridization assay at signal levels of over 600 times background.

Example 2:

In this experiment, two promoter-primers of identical nucleotide sequence were again used. The amplification and hybridization reaction conditions were essentially as in Example 1, with the following differences.

Each promoter-primer was synthesized with a T7 RNA polymerase promoter sequence of SEQ ID NO: 43 at the 5' end and a target hybridizing region of nucleotide sequence SEQ ID NO: 7 at the 3' end. One promoter-primer was synthesized with a free 3'-hydroxyl group and used at 2 pmol per reaction. The other promoter-primer was synthesized with a 3'-alkane diol modifying group and used at 13 pmol per reaction. The amplification conditions were as described in Example 1. After a two hour incubation at 42° C., twenty µl of the amplification reaction was assayed with an acridinium ester labeled probe of nucleotide sequence SEQ. ID. NO. 3. The reaction containing target nucleic acids was performed in triplicate; the negative control was performed in duplicate.

Table 2: Amplification of *C. trachomatis* RNA with amplification oligonucleotides having a target-binding nucleotide sequence of SEQ ID NO. 7, followed by detection with probe of nucleotide sequence SEQ ID NO: 3.

TABLE 2

| Amount of target added | RLU |
| --- | --- |
| 3 × 10$^{-19}$ moles | 195,920 |
|  | 171,617 |
|  | 57,195 |
| 0 moles | 1,772 |
|  | 2,596 |

Example 3:

This example demonstrates the amplification of *C. trachomatis* rRNA using a primer and promoter-primer of opposite orientation. The amplification and hybridization reaction conditions were essentially as described in Example 1 with the following modifications. One promoter-primer was synthesized having the T7 promoter sequence (SEQ ID NO:43) at the 5' end of a target-binding sequence region of nucleotide sequence SEQ ID NO: 4. This promoter-primer was used at 15 pmol per reaction in reactions containing 15 pmol of a primer having either SEQ ID NO: 5 or SEQ ID NO: 6. After a two hour incubation at 42° C., 20 μl of the reaction was assayed by hybridization using an acridinium ester labeled probe of SEQ. ID. NO. 1 and an unlabeled helper oligonucleotide of SEQ ID NO. 2 as described in Example 1. Target-containing reactions were performed in triplicate and a control reaction containing no target nucleic acid was performed in duplicate; results are reported below in RLU.

Table 3: Amplification of *C. trachomatis* rRNA using a promoter-primer of SEQ ID NO. 4 and a primer of SEQ ID NO. 5 or SEQ ID NO. 6, followed by detection with probe SEQ ID NO. 1.

TABLE 3

| Target | Primer | |
|---|---|---|
| | SEQ ID NO: 5 [+1428] | SEQ ID NO: 6 [+1428b] |
| 3 × 10⁻²¹ moles | 2,563,065 | 1,821,152 |
| *C. trachomatis* | 2,119,665 | 2,522,658 |
| RNA | 2,253,879 | 2,867,925 |
| No target added | 3,135 | 2,550 |
| | 3,010 | 2,831 |

Example 4:

The sensitivity of the amplification and detection system was determined by amplifying different amounts of *C. trachomatis* rRNA with 15 pmol of a promoter-primer consisting of SEQ ID NO:4 and having the T7 promoter sequence of Example 1 at the 5' end, and 15 pmol of a primer having SEQ ID NO:6. Amplification and hybridization reactions were essentially as described in Example 1. Following the amplification reaction, 100 μl of the amplification reaction was assayed with an acridinium ester labeled probe of SEQ ID NO:1 with unlabeled helper oligonucleotide of SEQ ID NO:2 as described in Example 1. Reaction were done either in duplicate or triplicate, and the results are reported below. Results are discussed in Example 5.

Table 4: Amplification of *C. trachomatis* RNA followed by detection with probe of SEQ ID No:1.

TABLE 4

| Amount of Target | RLU |
|---|---|
| 2 × 10⁻¹¹ moles | 2,028,207 |
| | 2,041,791 |
| 7 × 10⁻²² moles | 1,911,763 |
| | 2,016,830 |
| | 1,968,139 |
| 1 × 10⁻²² moles | 1,383,533 |
| | 1,025,833 |
| | 1,235,301 |
| 0 moles | 1,048 |
| | 1,077 |
| | 1,039 |

Example 5:

Amplification and hybridization reactions were performed essentially as in Example 1 with the following differences. *C. trachomatis* rRNA was amplified with a promoter-primer of SEQ. ID. NO. 7 and containing the T7 promoter sequence of Example 1 at the 5' end, and a primer of SEQ. ID. NO. 8. One microliter of the amplified nucleic acids were assayed with an acridinium ester-labeled probe of SEQ ID NO: 3.

Table 5: Amplification of *C. trachomatis* rRNA with a promoter-primer comprising SEQ ID NO. 7 and a primer consisting of SEQ ID NO: 8 followed by detection with probe consisting of SEQ ID NO: 3.

TABLE 5

| Amount of target added | RLU |
|---|---|
| 3 × 10⁻²¹ moles | 2,130,976 |
| | 1,999,462 |
| | 2,256,388 |
| 2 × 10⁻²¹ moles | 2,247,315 |
| | 1,538,319 |
| | 475,828 |
| 7 × 10⁻²² moles | 221,248 |
| | 149,353 |
| | 66,999 |
| 0 moles | 1,727 |
| | 1,691 |

The data obtained from this and the previous experiment show that *C. trachomatis* rRNA was detected following amplification with a promoter-primer having a target-binding region of SEQ. ID. NO. 4 containing a T7 promoter nucleotide sequence attached to the 5' end, paired with SEQ. ID. NO. 5 or SEQ. ID. NO. 6, followed by detection using labeled probe SEQ. ID. NO. 1 and helper oligonucleotide SEQ. ID. NO. 2, or with a primer SEQ. ID. NO. 7 containing a T7 promoter sequence, paired with SEQ. ID. NO. 8, followed by detection with probe SEQ. ID. NO. 3.

Example 6:

This example demonstrates the reactivity and specificity of the amplification and detection assay. Ribosomal RNA was isolated and purified from all known different *C. trachomatis* serovars. These rRNA species were amplified using 30 pmol of a promoter-primer of SEQ ID NO. 4 having the T7 promoter sequence of Example 1 covalently attached at the 5' end, and 30 pmol of a primer of SEQ ID NO. 6 per reaction. Single reactions containing 0.05 pg of rRNA and duplicate reactions containing 0.005 pg rRNA were performed using an amplification mixture as described in Example 1. Samples were heated to 95° C. for 5 minutes, cooled to 42° C. and 900 units of MMLV reverse transcriptase and 400 units of T7 RNA polymerase were added to each reaction. Following a 2 hour incubation at 42° C., 100 μl of the amplified nucleic acids were detected using the hybridization conditions described in Example 1 with an acridinium ester labeled hybridization assay probe of SEQ ID NO. 1 and an unlabeled helper probe of SEQ ID NO. 2. Results are reported in RLU.

Table 6: Amplification and detection of *C. trachomatis* rRNA from different serovars using a promoter primer of SEQ ID No:4 having a T7 promoter primer of SEQ ID NO:6, a labeled probe of SEQ ID NO:1 and a helper probe of SEQ ID NO:2.

TABLE 6

| C. trachomatis Serovar | ATCC No. | Amount rRNA $3 \times 10^{-20}$ moles | $3 \times 10^{-21}$ moles |
|---|---|---|---|
| A | VR 571B | 1,671,133 | 831,166 |
|   |   |   | 709,985 |
| B | VR 573 | 1,585,103 | 655,376 |
|   |   |   | 622,536 |
| C | VR 578 | 1,637,469 | 485,173 |
|   |   |   | 564,808 |
| D | VR 885 | 1,847,823 | 1,518,991 |
|   |   |   | 1,544,316 |
| E | VR 348B | 2,496,194 | 1,912,619 |
|   |   |   | 1,779,922 |
| F | VR 346 | 2,434,256 | 2,146,994 |
|   |   |   | 2,100,079 |
| G | VR 878 | 1,766,216 | 1,6461324 |
|   |   |   | 1,554,732 |
| H | VR 879 | 2,260,401 | 729,926 |
|   |   |   | 924,478 |
| I | VR 880 | 2,346,812 | 2,085,091 |
|   |   |   | 2,029,215 |
| J | VR 886 | 2,178,831 | 1,616,928 |
|   |   |   | 1,912,629 |
| K | VR 887 | 2,189,997 | 1,674,708 |
|   |   |   | 1,716,307 |
| LGV-1 | VR 901B | 2,158,983 | 2,065,327 |
|   |   |   | 2,011,899 |
| LGV-2 | VR 902B | 2,235,641 | 1,915,755 |
|   |   |   | 2,201,534 |
| LGV-3 | VR 903 | 2,173,648 | 1,963,084 |
|   |   |   | 1,939,574 |

The data show that all serovars of *C. trachomatis* were amplified and detected by the amplification oligonucleotides and probes. Moreover, there are thought to be about 2000 copies of 23S rRNA per cell; this works out to approximately $3\times10^{-21}$ moles of 23S rRNA per cell. Since this Example demonstrates that $3\times10^{-21}$ moles of rRNA can be detected using the amplification oligonucleotides of the present invention, it will be understood that these amplification oligonucleotides are capable of amplifying the rRNA target nucleotide sequences of one *Chlamydia trachomatis* organism per sample. This is distictly superior to the amplification sensitivity of primers directed to genomic (rather than ribosomal) nucleic acid sequences.

Example 7:

In this example, $3\times10^{-20}$ moles of purified RNA from either *C. trachomatis*, *C. pneumoniae* or *C. psittaci* was seperately amplified with the amplification oligonucleotides shown in Example 6, followed by detection with probe of SEQ ID NO. 1 as above. The data show that RNA from closely related species of Chlamydia were not detected under conditions permitting the detection of *C. trachomatis*. The results also indicate that the same amplification oligonucleotides which are capable of detecting every known serovar of *C. trachomatis* with exquiste sensitivity, as shown in Example 6, are also capable of discriminating between the nucleic acids of *C. trachomatis* and those of its closest known phylogenetic neighbors, *Chlamydia psittaci* and *Chlamydia pneumoniae*.

Table 7: Specificity of amplification with primers comprising SEQ ID No. 4 and 6, followed by detection with probe of SEQ ID NO. 1.

TABLE 7

| Target | ATCC NO. | RLU |
|---|---|---|
| C. pneumoniae | VR-1356 | 2,294 |
|   |   | 2,759 |
| C. psittaci | VR-656 | 1,506 |
|   |   | 1,541 |
| No target |   | 1,423 |
|   |   | 2,666 |
| C. trachomatis serovar J | VR-886 | 1,616,928 |
|   |   | 1,912,629 |

Example 8:

This example features one embodiment of the amplification oligonucleotides of the present invention which are able to bind to target nucleotide sequences of SEQ ID NOs 30–42. The examples that follow are intended to illustrate various embodients and uses of the oligonucleotides of the present invention, the scope of which is not limited to any such example or examples.

This example illustrates the amplification of a ribosomal RNA (rRNA) target nucleic acid by first producing a DNA template, and then amplifying the DNA template using a primer array and a 5'-exonuclease-deficient DNA polymerase. Production of the DNA template from rRNA and amplification of the template was carried out in the same reaction vessel containing the necessary reagents for production and amplification of the DNA template.

The primer array used in this example comprised thirteen primers. The primers were prepared by standard phosphoramidite chemistry as described above. Seven of the primers were complementary primers (with respect to the rRNA target). These primers have the following nucleic acid sequences:
SEQ. ID. NO: 17 CGCGTCTAGT CCTACTCAGG TGTTG
SEQ. ID. NO: 18 CCCCAGATTC AGACTAGG
SEQ. ID. NO: 19 CGGTCATTGA CTAGTATTTA GCCTT
SEQ. ID. NO: 20 TTTCTTCATA GTACTGGTTC ACT
SEQ. ID. NO: 21 ATTTCACTCC CTTAACAAGG GTT
SEQ. ID. NO: 22 TTGTAAGCTA CAGGTTTCAG GT
SEQ. ID. NO: 23 ACGGGCAATT GGTCTGCGAC C Six of the primers are sense primers (with respect to the rRNA target). These primers have the following nucleic acid sequences:
SEQ. ID. NO: 24 AGCAAAGACC CGGAGGTCCG AAT
SEQ. ID. NO: 25 GAATACATAG GTATGCAAAG CGA
SEQ. ID. NO: 26 CCTGCCGAAC TGAAACATCT TAGT
SEQ. ID. NO: 27 CAGAGGAAAA GAAATCGAAG AGAT
SEQ. ID. NO: 28 TGTAGGATTG AGGATAAAGG AT
SEQ. ID. NO: 29 GGACTCCTAG TTGAACACAT CTGGAAAGA.

Target 23S rRNA was obtained from *C. trachomatis* (See Glisin et al., *Biochemistry* 13:2633 (1974)), and diluted in buffer (50 mM Tris-HCl (pH 8.3), 37.5 mM KCl, 1.5 mM MgCl$_2$, 10 mM DTT). Different amounts of rRNA target were combined with the primers (7 picomoles each) in 20 µl of buffer (7% DMSO, 50 mM Tris-HCl (pH 8.3) 75 mM KCl, 3 mM MgCl$_2$, and 2 mM DTT) and incubated at 60° C. for 30 minutes to pre-hybridize the primers. The pre-hybridized primers were then exposed to 0.2 mMATP, 0.2 mM TTP, 0.2 mM GTP, 0.2 mM CTP, 200 units of Moloney Murine Leukemia Virus reverse transcriptase (MMLV-RT), and 2 units of a 5' exonuclease-deficient DNA polymerase obtained as a large subtilysin fragment of *Bacillus stearothermophilus* (Bst) DNA polymerase I. Amplification was carried out at 37° C. for 60 minutes, then at 60° C. for 120 minutes.

The amplification products were then denatured by incubation at 95° C. for 5 minutes and assayed using acridinium ester labeled probe according to Nelson et al., supra. Probe labeling with acridinium ester was carried out as described by Nelson et al., supra. The *C. trachomatis*-specific acridinium ester labeled probe was synthesized to have the nucleic acid sequence corresponding to SEQ ID NO: 44. The acridinium ester labeled probe ($2 \times 10^{-11}$ moles) was incubated with the amplification product at 60° C. for 15 minutes in 100 µl of hybridization buffer (100 mM lithium succinate (pH 5.2), 8% lithium dodecyl sulfate, 1.5 mM EDTA, and 1.5 mM EGTA). The acridinium ester present on unhybridized probe was then hydrolyzed by adding an alkaline solution (0.15M sodium tetraborate, pH 7.6, and 5% (v/v) TRITON® X-100) and incubating at 60° C. for 10 minutes. The remaining chemiluminescence was measured in a luminometer. The results shown in Table 8 demonstrate amplification of the target nucleic acid.

TABLE 8

| C. trachomatis rRNA (moles) | RLU (mean) |
|---|---|
| $4 \times 10^{-18}$ | 307893 |
| $4 \times 10^{-19}$ | 54771 |
| $4 \times 10^{-20}$ | 3644 |
| $4 \times 10^{-21}$ | 2354 |
| 0 | 2307 |

These data indicate that the use of amplification oligonucleotides of the present invention able to hybridize to SEQ ID NOs 30–42 in a primer array format results in an increase in nucleic acids bearing a *C. trachomatis* target nucleotide sequence. The example also demonstrates that, in this experiment, the primer array is at least able to detectably amplify as little as $4 \times 10^{-19}$ moles of target RNA.

Example 9:

This example illustrates the amplification of a *C. trachomatis* rRNA target nucleotide sequence present in a clinical specimen (human cervical swab specimen). The oligonucleotides, amplification procedure, and detection procedure used in this example were as described in Example 8. This example differs from Example 8 in the type of sample used, and in sample preparation.

Cervical swab samples were collected and suspended in a buffered solution containing an anionic detergent (60 mM phosphate buffer (pH 6.8), 6% lithium dodecyl sulfate, 2 mM EDTA, and 2 mM EGTA). The clinical specimen was given $10^{-18}$ moles of 23S *C. trachomatis* rRNA, and the sample allowed to hybridize with the amplification oligonucleotides comprising the primer array. The target nucleic acid was amplified and detected as described in Example 8. A successful amplification of target nucleic acid in the clinical sample was achieved; the amount of signal obtained in a hybridization assay of the amplified RNA-spiked sample was over 50-fold that seen in a similar mixture containing the clinical specimen but not spiked with *C. trachomatis* rRNA.

Example 10:

Primers of sequences SEQ ID NOS: 4 and 6 were designed to preferentially hybridize with *C. trachomatis* 23S rRNA over *C. psittaci* and *C. pneumoniae* 23S rRNA. To demonstrate the specificity of the primers for *C. trachomatis* in a different amplification format, they were tested as primers in the polymerase chain reaction (PCR). Each Chlamydia rRNA ($0.008 \times 10^{-15}$ mole) was incubated in a 20 µl of a solution containing 5 mM MgCl$_2$, 50 mM KCl, 10 mM Tris HCl, pH 8.3, 1 mM dTTP, 1 mM dATP, 1 mM dGTP, 1 mM dCTP, 20 U RNasin, 50 U of MMLV reverse transcriptase and 100 pmol of a primer complementary to *C. trachomatis* rRNA of SEQ ID NO: 103 GTCGCCTGGG CCATTTCTCT GCGGCCCCCC GGGG designed to hybridize downstream of the binding site for a primer of SEQ ID NO:4 at 42° C. for 15 minutes, then at 95° C. for 10 minutes, and finally at 80° C. for 3 minutes. To this solution was added 80 µl of a solution containing 25 mM MgCl$_2$, 50 mM KCL, 10 mM Tris HCl pH 8.3, 2.5 U Taq polymerase, 50 pmol of a promoter-primer having a T7 promoter sequence of SEQ ID NO:43 at the 5' end and a 3' primer sequence of SEQ ID NO:4, and 50 pmol of a primer of SEQ ID NO:6. As a control, a primer and promoter-primer pair having target binding regions complementary to *C. pneumoniae* rRNA sequence regions were used in a similar amplification format; the promoter region of the promoter-primer had the same T7 promoter sequence at the 5' end. Because the nucleic acid amplification format chosen was the PCR, the promoter sequences were not necessary for the amplification reaction. The reaction mixtures were thermocycled 35 times at 55° C. for 0.5 minute, 72° C. for 1 minute and 95° C. for 1 minute, followed by a final 72° C. incubation for 7 minutes and cooling to 4° C. prior to hybridization or gel analysis. Twenty µl of each reaction mixture was analyzed by electrophoresis on a 2% agarose gel using Tris borate EDTA buffer, followed by ethidium bromide staining. Nucleic acids were visualized under ultraviolet light. Results are summarized as follows:

Table 9: Target specificity of amplification oligonucleotides having SEQ. ID. NOs 4 and 6 using PCR.

TABLE 9

| Target rRNA | Specificity | Gel Band Observed |
|---|---|---|
| C. trachomatis | C. trachomatis | yes |
| C. pneumoniae | C. trachomatis | no |
| C. psittaci | C. trachomatis | no |
| C. pneumoniae | C. pneumoniae/C. psittaci | yes |
| C. psittaci | C. pneumoniae/C. psittaci | yes |

These results demonstrate that under selective hybridization conditions the *C. trachomatis* primers having SEQ. ID. NOs: 4 and 6 will specifically amplify *C. trachomatis* nucleic acids, while not amplifying *C. pneumoniae* or *C. psittaci* rRNA sequences.

Example 11:

The sensitivity of an amplification and detection system directed to *C. trachomatis* 16S rRNA nucleotide sequences was illustrated by amplifying different amounts of *C. trachomatis* rRNA with 30 pmol of a promoter-primer having the nucleotide sequence SEQ. ID. NO: 50 as the 3' portion and having the T7 promoter sequence SEQ. ID. NO: 106 at the 5' end, and 30 pmol of a primer having SEQ ID NO. 44. Amplification and hybridization reactions were otherwise as described in Example 1. Following the amplification reaction, 20 µl of the amplification reaction was assayed with a mixture of an acridinium ester-labeled probe having SEQ ID NO. 46 and an unlabeled helper oligonucleotide of SEQ ID NO: 48 as described in Example 1. Reactions were done in triplicate; the results are reported below.

Table 10: Amplification of C. trachomatis RNA with 16S rRNA-directed oligonucleotides of SEQ ID NOS 43 End 44 followed by detection with probe of SEQ ID NO: 46.

TABLE 10

| Amount of Target | RLU |
|---|---|
| $2 \times 10^{-22}$ moles | 688,135 |
|  | 200,365 |
|  | 760,817 |
| $8 \times 10^{-23}$ moles | 61,804 |
|  | 531,864 |
|  | 1,081,653 |
| 0 moles | 506 |
|  | 443 |
|  | 443 |

The results demonstrate the ability of probes and amplification oligonucleotides directed to C. trachomatis 16S rRNA to amplify and detect the presence of C. trachomatis nucleic acids in solution at a level approaching the rRNA contained in one Chalmydia trachomatis cell.

Example 12:

The specificity of the amplication and detection system directed to Chlamydia trachomatis 16S rRNA was demonstrated by amplifying either cell lysates or purified RNA from various organisms with the amplification oligonucleotides described in Example 11. The organisms chosen to be detected are among those commonly isolated from the human urogenital tract as well as organisms that represent a phylogenetic cross-section. Each sample contained either cell lysates representing at least 250,000 cells or $2\times10^{-15}$ moles of purified RNA. This was added to an amplification reaction as described in Example 11. The entire 100 microliter reaction was assayed by nucleic acid hybridization as described in Example 1 using probe SEQ ID NO. 46 and an unlabeled helper probe of SEQ ID NO. 48. Results shown in Tables 11 and 12 below are the average of three replicates.

TABLE 11

| Urogenital tract organism | ATCC NO. | RLU |
|---|---|---|
| Bacteroides fragilis | 23745 | 2,983 |
| Bacteroides ureolyticus | 43605 | 3,374 |
| Candida albicans | 18804 | 3,078 |
| *Chlamydia trachomatis | VR-886 | 2,660,682 |
| Clostridium perfringens | 13124 | 4,422 |
| Eikenella corrodens | 23834 | 3,615 |
| Gardnerella vaginalis | 14018 | 2,909 |
| Haemphilus influenzae | 9795 | 3,020 |
| Lactobacillus acidophilus | 4356 | 2,976 |
| Listeria monocytogenes | 35152 | 2,861 |
| Mycobacterium smegmatis | 14468 | 4,228 |
| °Mycoplasma hominis | 14027 | 2,973 |
| Neisseria gonorrhoeae | 19424 | 2,714 |
| Peptostreptococcus anaerobius | 27337 | 6,781 |
| Propionibacterium acnes | 6919 | 3,671 |
| Staphylococcus aureus | 12598 | 6,107 |
| Staphylococcus epidermidis | 12228 | 2,972 |
| Torulopsis glabrata | 2001 | 2,905 |
| °Ureaplasma urealyticum | 27618 | 2,927 |

*100,000 IFU/assay
°rRNA

TABLE 12

| Phylogenetic cross section | ATCC NO. | RLU |
|---|---|---|
| Bacillus subtilis | 6051 | 2,884 |
| Chlamydia pneumoniae[1] | VR1356 | 3,474 |

TABLE 12-continued

| Phylogenetic cross section | ATCC NO. | RLU |
|---|---|---|
| Chlamydia psittaci[2] | VR656 | 7,764 |
| Citrobacter freundii | 6750 | 2,839 |
| Corynebacterium xerosis | 19411 | 2,352 |
| Deinococcus radiodurans | 35073 | 2,954 |
| Enterobacter aerogenes | 13048 | 2,941 |
| Escherichia coli | 10798 | 3,021 |
| Klebsiella pneumoniae | 23357 | 2,983 |
| Legionella pneumophila | 33152 | 2,967 |
| Pseudomonas aeruginosa | 10145 | 3,042 |
| Streptococcus pyogenes | 12344 | 2,935 |
| Yersinia enterocolitica | 9610 | 2,968 |
| No target |  | 4,034 |

[1] = $2 \times 10^{-14}$ moles rRNA,
[2] = $2 \times 10^{-13}$ moles rRNA

Example 13:

Primers of sequences SEQ ID NOs. 44 and 50 were tested in a polymerase chain reaction (PCR) format using MMLV reverse transcriptase. Chlamydia rRNA ($2\times10^{-16}$ mole) was incubated in a 20 µl of a solution containing 5 mM MgCl$_2$, 50 mM KCl, 10 mM Tris HCl, pH 8.3, 1 mM dTTP, 1 mM dATP, 1 mM dGTP, 1 mM dCTP, 20 U RNasin, 50 U of MMLV reverse transcriptase and 1 nmole random nucleotide hexamers [purchased from Boehringer Mannheim] at 42° C. for 15 minutes, then at 95° C. for 10 minutes, and finally at 80° C. for 3 minutes. To this solution was added 80 µl of a solution containing 1.25 mM MgCl$_2$, 50 mM KCL, 10 mM Tris HCl pH 8.3, 2.5 U Taq polymerase, 50 pmol of a promoter-primer having a T7 promoter sequence of SEQ ID NO:106 at the 5' end and a target-binding region of sequence SEQ ID NO:50 at the 3' end, and 50 pmol of a primer of SEQ ID NO:44. In the PCR format, the promoter sequence is not necessary to obtain amplification. The reaction mixtures were cycled 35 times at 55° C. for 0.5 minute, 72° C. for 1 minute, and 95° C. for 1 minute, followed by a final 72° C. incubation for 7 minutes and cooling to 4° C. prior to hybridization or gel analysis. Twenty µl of each reaction mixture was analyzed by electrophoresis on a 2% agarose gel using Tris borate EDTA buffer, followed by nucleic acid visualization using ethidium bromide staining. An amplicon band of the expected size was observed with all three species of Chlamydia; C. trachomatis, C. psittaci, and C. pneumoniae.

The reaction mixtures were then assayed by hybridization with an acridinium ester-labeled probe of SEQ ID NO 46 and helper probe of SEQ ID NO. 48. The results are as shown in the following Table 13.

TABLE 13

| RNA target | ATCC NO. | RLU |
|---|---|---|
| C. trachomatis | VR-886 | 1,597,135 |
| C. pneumoniae | VR-1356 | 975 |
| C. psittaci | VR-656 | 1,004 |

These results demonstrate the ability of the probe/helper oligonucleotide combination to specifically detect Chlamydia trachomatis even in a sample containing a large amount of RNA from closely related organisms.

Example 14:

This example demonstrates the ability of promoter-primers of a single nucleotide sequence to amplify Chlamydia trachomatis 16S rRNA sequences. In this experiment, varied amounts of purified *C. trachomatis* (ATCC No. VR-886) rRNA were amplified with two oligonucleotides of negative sense having a nucleotide sequence complementary to *C. trachomatis* 16S rRNA. Two promoter-primers were synthesized, each containing a T7 promoter nucleotide sequence of SEQ ID NO 106 covalently attached to the 5' end of a oligonucleotide of nucleotide sequence SEQ ID NO 50.

One of the promoter-primers was synthesized with a free 3'-terminal hydroxyl group, and was used at two pmol per reaction. The second promoter-primer was synthesized with an alkane diol group covalently bound to the 3' end to block or lessen the amount of primer extension, and was used at 13 pmol per reaction. The amplification reaction and hybridization assay was performed as described in Example 1. The acridinium ester labeled probe consisted of a nucleotide sequence SEQ ID NO. 46, and was used with an unlabeled helper probe of sequence SEQ ID NO. 48. Results are the average of triplicate reactions for each condition.

Table 14: Amplification of 16S rRNA using a mixture of blocked and unblocked promoter-primers having a T7 promoter of SEQ ID NO 106 and a target binding region of SEQ ID NO 50.

TABLE 14

| Amount of target RNA add | RLU |
|---|---|
| $2 \times 10^{-20}$ moles | 273,125 |
| $3 \times 10^{-21}$ moles | 74,594 |
| $2 \times 10^{-21}$ moles | 18,133 |
| 0 moles | 934 |

The embodiments shown in the various examples described above confirm that the oligonucleotides herein described are capable of amplifying and/or detecting *Chlamydia trachomatis* nucleic acids, and can be used in an assay to distinguish *Chlamydia trachomatis* from its known nearest phylogenetic neighbors. None of the examples described herein are intended to limit the present invention to the embodiments of the preceding disclosure; additional embodiments are within the following claims.

What is claimed is:

1. A method off detecting the presence of nucleic acids in a sample comprising:
   a) contacting said sample with a first oligonucleotide which hybridizes to rRNA or rDNA of *Chlamydia trachomatis* and not to rRNA or rDNA of non-Chlamydia bacteria under hybridization conditions corresponding to 0.8M monovalent cation at 60° C. for 15 minutes wherein said oligonucleotide is complementary to a region of *Chlamydia trachomatis* rRNA or a region of DNA encoding said rRNA and has a nucleotide sequence selected from the group consisting of:
      i) SEQ ID NO:1, and
      ii) RNA equivalents thereof having uracil substitutes for thymine,
   and conservatively modified variants thereof, and a second oligonucleotide which hybridizes to rRNA or rDNA of *Chlamydia trachomatis* under said conditions and has a nucleotide sequence selected from the group consisting of:
      iii) SEQ ID NO:2, and
      iv) RNA equivalents thereof having uracil substitutes for thymine,
   and conservatively modified versions thereof,
   b) imposing said hybridization conditions on said sample and said first and second oligonucleotides to allow the oligonucleotides to hybridize to nucleic acids encoding *Chlamydia trachomatis* rRNA or rDNA sequences, if present, to form a stable hybrid, and
   c) detecting said hybrid, if present in said sample, as an indication of the presence of *Chlamydia trachomatis* nucleic acids in the sample.

2. A method of detecting the presence of *Chlamydia trachomatis* nucleic acids in a sample comprising:
   a) contacting said sample with a first oligonucleotide which hybridizes to rRNA or rDNA of *Chlamydia trachomatis* and not to rRNA or rDNA of non-Chlamydia bacteria under hybridization conditions corresponding to 0.8M monovalent cation at 60° C. for 15 minutes wherein said oligonucleotide is complementary to a region of *Chlamydia trachomatis* rRNA or a region of DNA encoding said rRNA and has a nucleotide sequence selected from the group consisting of:
      i) SEQ ID NO:46, and
      ii) RNA equivalents thereof having uracil substitutes for thymine,
   and conservatively modified variants thereof, and a second oligonucleotide which hybridizes to rRNA or rDNA of *Chlamydia trachomatis* under said conditions and has a nucleotide sequence selected from the group consisting of:
      iii) SEQ ID NO:48, and
      iv) RNA equivalents thereof having uracil substitutes for thymine,
   and conservatively modified versions thereof,
   b) imposing said hybridization conditions on said sample and said first and second oligonucleotides to allow the oligonucleotides to hybridize to nucleic acids encoding *Chlamydia trachomatis* rRNA or rDNA sequencers, if present, to form a stable hybrid, and
   c) detecting said hybrid, if present in said sample, as an indication of the presence of *Chlamydia trachomatis* nucleic acids in the sample.

3. A method for the detection of *Chlamydia trachomatis* comprising:
   a) amplifying *Chlamydia trachomatis* nucleic acids with at least one amplification oligonucleotide that will bind to or cause polymerization through a region of *Chlamydia trachomatis* nucleic acids of between 22 and 100 nucleotides, said region having a nucleotide sequence selected from the group consisting of:
      i) SEQ ID NO: 12,
      ii) SEQ ID NO: 5,
      iii) SEQ ID NO: 6,
      iv) SEQ ID NO: 11,
      v) RNA equivalents of these sequences having uracil substituted for thymine, and
   b) detecting the amplified nucleic acids with an oligonucleotide hybridization assay probe which will specifically hybridize with *Chlamydia trachomatis* nucleic acids over nucleic acids of *Chlamydia psittaci* and *Chlamydia pneumoniae* under hybridization conditions corresponding to 0.8M monovalent cation at 60° C. for 15 minutes.

4. The method of claim 3 wherein said amplification oligonucleotides are able to hybridize with *Chlamydia trachomatis* nucleic acids under hybridization conditions not promoting the hybridization of said oligonucleotides to nucleic acids of *Chlamydia psittaci* and *Chlamydia pneumoniae*.

5. The method of claim 4 wherein one or more amplification oligonucleotides have nucleotide sequences selected from the group consisting of SEQ ID NO: 4, SEQ ID NO: 6, and conservatively modified varients thereof.

6. The method of claim 3 wherein one or more of said amplification oligonucleotides have a 5' non-complementary nucleotide sequence which is capable of initiating RNA synthesis by an RNA polymerase.

7. The method of claim 6 wherein one or more of said amplification oligonucleotides have a 5' non-complementary nucleotide sequence substantially similar to a nucleotide sequence which is selected from the group consisting of:
   a) SEQ ID NO: 43,
   b) SEQ ID NO: 106,
   c) SEQ ID NO: 104,
   d) SEQ ID NO: 107, and
   e) RNA versions thereof having uracil substituted for thymine.

8. The method of claim 6 wherein said amplifying step comprises the use of at least one population of amplification oligonucleotides of the same or substantially similar nucleotide sequence wherein a subpopulation of said amplification oligonucleotides consists of oligonucleotides having modifications to their 3' termini which reduce or eliminate the ability of a nucleic acid polymerase to extend said 3' termini.

9. The method of claim 3 wherein said amplifying step comprises the use of at least two amplification oligonucleotides, one or more of which has a nucleotide sequence substantially similar to a nucleotide sequence selected from the group consisting of:
a) SEQ ID NO: 4,
b) SEQ ID NO: 5,
c) SEQ ID NO: 6, and
d) RNA equivalents thereof having uracil substituted in place of thymine,
wherein said one or more oligonucleotides may have a 5' non-complementary sequence which is capable of initiating RNA synthesis by an RNA polymerase.

10. The method of claim 3 wherein said amplifying step comprises the use of at least two different amplification oligonucleotides, each having a nucleotide sequence substantially similar to a nucleotide sequence selected from the group consisting of:
a) SEQ ID NO: 4,
b) SEQ ID NO: 5,
c) SEQ ID NO: 6, and
d) RNA equivalents thereof having uracil substituted in place of thymine, and
wherein said different oligonucleotides may have a 5' non-complementary sequence which is capable of initiating RNA synthesis by an RNA polymerase, provided that none of said different amplification oligonucleotides is substantially similar to the same SEQ ID NO.

11. The method of claim 3 wherein the hybridization assay probe has a nucleotide sequence substantially similar to a nucleotide sequence selected from the group consisting of:
a) SEQ ID NO: 1, and
b) RNA equivalents thereof having uracil substituted for thymine.

12. The method of claim 3 wherein said detecting step further comprises the addition of a helper oligonucleotide having a nucleotide sequence substantially similar to a nucleotide sequence selected from the group consisting of SEQ. ID. NO: 2 and RNA equivalents thereof having uracil substituted for thymine.

13. A method for the detection of *Chlamydia trachomatis* comprising:
a) amplifying *Chlamydia trachomatis* nucleic acids with at least one amplification oligonucleotide that will bind to or cause polymerization through a region of *Chlamydia trachomatis* nucleic acids of between 22–100 nucleotides, said region having a nucleotide sequence selected from the group consisting of:
i) SEQ ID NO: 2,
ii) SEQ ID NO: 4,
iii) SEQ ID NO: 13,
iv) SEQ ID NO: 14, and
v) RNA equivalents of these sequences having uracil substituted for thymine, and
b) detecting the amplified nucleic acids with an oligonucleotide hybridization assay probe which will specifically hybridize with *Chlamydia trachomatis* nucleic acids over nucleic acids of *Chlamydia psittaci* and *Chlamydia pneumoniae* under hybridization conditions corresponding to 0.8M monovalent cation at 60° C. for 15 minutes.

14. The method of claim 13 wherein said amplification oligonucleotides are able to hybridize with *Chlamydia trachomatis* nucleic acids under hybridization conditions not promoting the hybridization of said oligonucleotides to nucleic acids of *Chlamydia psittaci* and *Chlamydia pneumoniae*.

15. The method of claim 14 wherein one or more amplification oligonucleotides have nucleotide sequences selected from the group consisting of SEQ ID NO: 4, SEQ ID NO: 6, and conservatively modified varients thereof.

16. The method of claim 13 wherein one or more of said amplification oligonucleotides have a 5' non-complementary nucleotide sequence which is capable of initiating RNA synthesis by an RNA polymerase.

17. The method of claim 16 wherein one or more of said amplification oligonucleotides have a 5' non-complementary nucleotide sequence substantially similar to a nucleotide sequence which is selected from the group consisting of:
a) SEQ ID NO: 43,
b) SEQ ID NO: 106,
c) SEQ ID NO: 104,
d) SEQ ID NO: 107, and
e) RNA versions thereof having uracil substituted for thymine.

18. The method of claim 16 wherein said amplifying step comprises the use of at least one population of amplification oligonucleotides of the same or substantially similar nucleotide sequence wherein a subpopulation of said amplification oligonucleotides consists of oligonucleotides having modifications to their 3' termini which reduce or eliminate the ability of a nucleic acid polymerase to extend said 3' termini.

19. The method of claim 13 wherein said amplifying step comprises the use of two or more amplification oligonucleotides, at least one of which has a nucleotide sequence substantially similar to a nucleotide sequence selected from the group consisting of:
a) SEQ ID NO: 4,
b) SEQ ID NO: 5,
c) SEQ ID NO: 6, and
d) RNA equivalents thereof having uracil substituted in place of thymine.

20. The method of claim 13 wherein said amplifying step comprises the use of at least two different amplification oligonucleotides, each having a nucleotide sequence substantially similar to a nucleotide sequence selected from the group consisting of:
a) SEQ ID NO: 4,
b) SEQ ID NO: 5,
c) SEQ ID NO: 6, and
d) RNA equivalents thereof having uracil substituted in place of thymine,
provided that none of said different amplification oligonucleotides is substantially similar to the same SEQ ID NO.

21. The method of claim 13 wherein the hybridization assay probe has a nucleotide sequence substantially similar to a nucleotide sequence selected from the group consisting of:
a) SEQ ID NO: 9, and b) RNA equivalents thereof having uracil substituted for thymine.

22. The method of claim 13 wherein said detecting step further comprises the addition of a helper oligonucleotide.

23. A method for the detection of *Chlamydia trachomatis* comprising:
   a) amplifying *Chlamydia trachomatis* nucleic acids with at least one amplification oligonucleotide that will bind to or cause polymerization through a region of *Chlamydia trachomatis* nucleic acids of between 24–100 nucleotides, said region having a nucleotide sequence selected from the group consisting of:
      i) SEQ ID NO: 3,
      ii) SEQ ID NO: 8,
      iii) SEQ ID NO: 15, and
      iv) RNA equivalents of these sequences having uracil substituted for thymine, and
   b) detecting the amplified nucleic acids with an oligonucleotide hybridization assay probe which will specifically hybridize with *Chlamydia trachomatis* nucleic acids over nucleic acids of *Chlamydia psittaci* and *Chlamydia pneumoniae* under hybridization conditions corresponding to 0.8M monovalent cation at 60° C. for 15 minutes.

24. The method of claim 23 wherein one or more of said amplification oligonucleotides have a 5' non-complementary nucleotide sequence which is capable of initiating RNA synthesis by an RNA polymerase.

25. The method of claim 24 wherein one or more of said amplification oligonucleotides have a 5' non-complementary nucleotide sequence substantially similar to a nucleotide sequence which is selected from the group consisting of:
   a) SEQ ID NO: 43,
   b) SEQ ID NO: 106,
   c) SEQ ID NO: 104,
   d) SEQ ID NO: 107, and
   e) RNA versions thereof having uracil substituted for thymine.

26. The method of claim 24 wherein said amplifying step comprises the use of at least one population of amplification oligonucleotides of the same or substantially similar nucleotide sequence wherein a subpopulation of said amplification oligonucleotides consists of oligonucleotides having modifications to their 3' termini which reduce or eliminate the ability of a nucleic acid polymerase to extend said 3' termini.

27. The method of claim 23 wherein said amplifying step comprises the use of two or more amplification oligonucleotides, at least one of which has a nucleotide sequence substantially similar to a nucleotide sequence selected from the group consisting of:
   a) SEQ ID NO: 7,
   b) SEQ ID NO: 8, and
   c) RNA equivalents thereof having uracil substituted in place of thymine.

28. The method of claim 23 wherein said amplifying step comprises the use of two different amplification oligonucleotides, each having a nucleotide sequence substantially similar to a nucleotide sequence selected from the group consisting of:
   a) SEQ ID NO: 7,
   b) SEQ ID NO: 8, and
   c) RNA equivalents thereof having uracil substituted in place of thymine,
   provided that neither of said different amplification oligonucleotides is substantially similar to the same SEQ ID NO.

29. The method of claim 23 wherein the hybridization assay probe has a nucleotide sequence substantially similar to a nucleotide sequence selected from the group consisting of:
   a) SEQ ID NO: 10, and
   b) RNA equivalents thereof having uracil substituted for thymine.

30. The method of claim 23 wherein said detecting step further comprises the addition of a helper oligonucleotide.

31. A method for the detection of *Chlamydia trachomatis* comprising:
   a) amplifying *Chlamydia trachomatis* nucleic acids with at least one amplification oligonucleotide that will bind to or cause polymerization through a region of *Chlamydia trachomatis* nucleic acids of between 24–100 nucleotides, said region having a nucleotide sequence selected from the group consisting of:
      i) SEQ ID NO: 10,
      ii) SEQ ID NO: 7,
      iii) SEQ ID NO: 16, and
      iv) RNA equivalents thereof having uracil substituted for thymine, and
   b) detecting the amplified nucleic acids with an oligonucleotide hybridization assay probe which will specifically hybridize with *Chlamydia trachomatis* nucleic acids over nucleic acids of *Chlamydia psittaci* and *Chlamydia pneumoniae* under hybridization conditions corresponding to 0.8M monovalent cation at 60° C. for 15 minutes.

32. The method of claim 31 wherein one or more of said amplification oligonucleotides have a 5' non-complementary nucleotide sequence which is capable of initiating RNA synthesis by an RNA polymerase.

33. The method of claim 32 wherein one or more of said amplification oligonucleotides have a 5' non-complementary nucleotide sequence substantially similar to a nucleotide sequence which is selected from the group consisting of:
   a) SEQ ID NO: 43,
   b) SEQ ID NO: 106,
   c) SEQ ID NO: 104,
   d) SEQ ID NO: 107, and
   e) RNA versions thereof having uracil substituted for thymine.

34. The method of claim 32 wherein said amplifying step comprises the use of at least one population of amplification oligonucleotides of the same or substantially similar nucleotide sequence wherein a subpopulation of said amplification oligonucleotides consists of oligonucleotides having modifications to their 3' termini which reduce or eliminate the ability of a nucleic acid polymerase to extend said 3' termini.

35. The method of claim 31 wherein said amplifying step comprises the use of two or more amplification oligonucleotides, at least one of which has a nucleotide sequence substantially similar to a nucleotide sequence selected from the group consisting of:
   a) SEQ ID NO: 7,
   b) SEQ ID NO: 8, and
   c) RNA equivalents thereof having uracil substituted in place of thymine.

36. The method of claim 31 said amplifying step comprises the use of two different amplification oligonucleotides, each having a nucleotide sequence substantially similar to a nucleotide sequence selected from the group consisting of:

a) SEQ ID NO: 7, b) SEQ ID NO: 8, and c) RNA equivalents thereof having uracil substituted in place of thymine, provided that none of said different amplification oligonucleotides is substantially similar to the same SEQ ID NO.

37. The method of claim 31 wherein the hybridization assay probe has a nucleotide sequence substantially similar to a nucleotide sequence selected from the group consisting of:

a) SEQ ID NO: 3, and b) RNA equivalents thereof having uracil substituted for thymine.

38. The method of claim 31 wherein said detecting step further comprises the addition of a helper oligonucleotide.

39. A method for the detection of *Chlamydia trachomatis* comprising:

a) amplifying *Chlamydia trachomatis* nucleic acids with at least one amplification oligonucleotide that will bind to or cause polymerization through a region of *Chlamydia trachomatis* nucleic acids of between 27–100 nucleotides, said region having a nucleotide sequence selected from the group consisting of:
i) SEQ ID NO: 44,
ii) SEQ ID NO: 51,
iii) SEQ ID NO: 48, and
iv) RNA equivalents of these sequences having uracil substituted for thymine, and b) detecting the amplified nucleic acids with an oligonucleotide hybridization assay probe which will specifically hybridize with *Chlamydia trachomatis* nucleic acids over nucleic acids of *Chlamydia psittaci* and *Chlamydia pneumoniae* under hybridization conditions corresponding to 0.8M monovalent cation at 60° C. for 15 minutes.

40. The method of claim 39 wherein one or more of said amplification oligonucleotides have a 5' non-complementary nucleotide sequence which is capable of initiating RNA synthesis by an RNA polymerase.

41. The method of claim 40 wherein one or more of said amplification oligonucleotides have a 5' non-complementary nucleotide sequence substantially similar to a nucleotide sequence which is selected from the group consisting of:

a) SEQ ID NO: 43, b) SEQ ID NO: 106, and c) RNA versions thereof having uracil substituted for thymine.

42. The method of claim 40 wherein said amplifying step comprises the use of at least one population of amplification oligonucleotides of the same or substantially similar nucleotide sequence wherein a subpopulation of said amplification oligonucleotides consists of oligonucleotides having modifications to their 3' termini which reduce or eliminate the ability of a nucleic acid polymerase to extend said 3' termini.

43. The method of claim 39 wherein said amplifying step comprises the use of two or more amplification oligonucleotides, at least one of which has a nucleotide sequence substantially similar to a nucleotide sequence selected from the group consisting of:

a) SEQ ID NO: 44, b) SEQ ID NO: 50, and c) RNA equivalents thereof having uracil substituted in place of thymine.

44. The method of claim 39 wherein said amplifying step comprises the use of two different amplification oligonucleotides, each having a nucleotide sequence substantially similar to a nucleotide sequence selected from the group consisting of:

a) SEQ ID NO: 44, b) SEQ ID NO: 50, and c) RNA equivalents thereof having uracil substituted in place of thymine, provided that none of said different amplification oligonucleotides is substantially similar to the same SEQ ID NO.

45. The method of claim 39 wherein the hybridization assay probe has a nucleotide sequence substantially similar to a nucleotide sequence selected from the group consisting of:

a) SEQ ID NO: 47, and b) RNA equivalents thereof having uracil substituted for thymine.

46. The method of claim 39 wherein said detecting step further comprises the use of a helper oligonucleotide having a nucleotide sequence selected from the group consisting of:

a) SEQ ID NO: 48, and b) RNA equivalents thereof having uracil substituted for thymine.

47. A method for the detection of *Chlamydia trachomatis* comprising:

a) amplifying *Chlamydia trachomatis* nucleic acids with at least one amplification oligonucleotide that will bind to or cause polymerization through a region of *Chlamydia trachomatis* nucleic acids of between 27–100 nucleotides, said region having a nucleotide sequence selected from the group consisting of:
i) SEQ ID NO: 49,
ii) SEQ ID NO: 45,
iii) SEQ ID NO: 50, and
iv) RNA equivalents of these sequences having uracil substituted for thymine, and b) detecting the amplified nucleic acids with an oligonucleotide hybridization assay probe which will specifically hybridize with *Chlamydia trachomatis* nucleic acids over nucleic acids of *Chlamydia psittaci* and *Chlamydia pneumoniae* under hybridization conditions corresponding to 0.8M monovalent cation at 60° C. for 15 minutes.

48. The method of claim 47 wherein one or more of said amplification oligonucleotides have a 5' non-complementary nucleotide sequence which is capable of initiating RNA synthesis by an RNA polymerase.

49. The method of claim 48 wherein one or more of said amplification oligonucleotides have a 5' non-complementary nucleotide sequence substantially similar to a nucleotide sequence which is selected from the group consisting of:

a) SEQ ID NO: 43, b) SEQ ID NO: 106, c) RNA versions thereof having uracil substituted for thymine.

50. The method of claim 48 wherein said amplifying step comprises the use of at least one population of amplification oligonucleotides of the same or substantially similar nucleotide sequence wherein a subpopulation of said amplification oligonucleotides consists of oligonucleotides having modifications to their 3' termini which reduce or eliminate the ability of a nucleic acid polymerase to extend said 3' termini.

51. The method of claim 47 wherein said amplifying step comprises the use of two or more amplification oligonucleotides, at least one of which has a nucleotide sequence substantially similar to a nucleotide sequence selected from the group consisting of:
 a) SEQ ID NO: 44,
 b) SEQ ID NO: 50, and
 c) RNA equivalents thereof having uracil substituted in place of thymine.

52. The method of claim 47 wherein said amplifying step comprises the use of two different amplification oligonucleotides, each having a nucleotide sequence substantially similar to a nucleotide sequence selected from the group consisting of:
 a) SEQ ID NO: 44,
 b ) SEQ ID NO: 50, and
 c) RNA equivalents thereof having uracil substituted in place of thymine, provided that none of said different amplification oligonucleotides is substantially similar to the same SEQ ID NO.

53. The method of claim 47 wherein the hybridization assay probe has a nucleotide sequence substantially similar to a nucleotide sequence selected from the group consisting of:
 a) SEQ ID NO: 46, and
 b) RNA equivalents thereof having uracil substituted for thymine.

54. The method of claim 47 wherein said detecting step further comprises the addition of a helper oligonucleotide.

* * * * *